United States Patent
Reitblat et al.

(10) Patent No.: US 10,507,046 B2
(45) Date of Patent: Dec. 17, 2019

(54) TISSUE RETRACTION AND VERTEBRAL DISPLACEMENT DEVICES, SYSTEMS, AND METHODS FOR POSTERIOR SPINAL FUSION

(71) Applicant: Stryker European Holdings I, LLC, Kalamazoo, MI (US)

(72) Inventors: Abram Reitblat, Monroe, NY (US); Steven Krause, Oakland, NJ (US); Douglas G. Pedrick, Newburgh, NY (US); David Talijan, Mahwah, NJ (US); Erika Corbin, Mahwah, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 63 days.

(21) Appl. No.: 15/466,302

(22) Filed: Mar. 22, 2017

(65) Prior Publication Data
US 2017/0189080 A1 Jul. 6, 2017

Related U.S. Application Data

(62) Division of application No. 14/569,013, filed on Dec. 12, 2014, now Pat. No. 9,622,795.
(Continued)

(51) Int. Cl.
*A61B 17/02* (2006.01)
*A61B 17/00* (2006.01)
(Continued)

(52) U.S. Cl.
CPC ...... *A61B 17/7077* (2013.01); *A61B 17/0206* (2013.01); *A61B 17/708* (2013.01);
(Continued)

(58) Field of Classification Search
CPC ............ A61B 17/7077; A61B 17/7079; A61B 17/0206; A61B 2017/0256
See application file for complete search history.

(56) References Cited

U.S. PATENT DOCUMENTS

| 3,997,138 A | 12/1976 | Crock et al. |
| 4,382,438 A | 5/1983 | Jacobs |

(Continued)

FOREIGN PATENT DOCUMENTS

| DE | 19726754 A1 | 2/1999 |
| DE | 10027988 A1 | 1/2002 |

(Continued)

OTHER PUBLICATIONS

Charles Hartjen; The Atavi System, Surgical Technique Brochure. Endius, p. 1-17, undated.
(Continued)

*Primary Examiner* — Ellen C Hammond
(74) *Attorney, Agent, or Firm* — Lerner, David, Littenberg, Krumholz & Mentlik, LLP

(57) ABSTRACT

Devices for retracting tissue during a minimally-invasive, posterior spinal fusion procedure include a blade positionable along a passageway device connected to a connecting element implanted in a vertebra of the spine, such that the blade covers at least a portion of a longitudinal opening of the passageway device. The blade may be coupled to the passageway device by receiving the passageway device with a receiving portion. Systems for displacing the vertebrae of the spine include first and second extenders, the distal ends of each of which are configured to engage the connecting elements. Each extender may include a shaft configured to be securely engaged within a cage of the respective connecting element. The devices and systems of the present invention may be used in connection with an interbody fusion technique performed through an opening extending
(Continued)

between the passageway devices, and an intermediate retractor blade may provide additional tissue retraction.

20 Claims, 14 Drawing Sheets

Related U.S. Application Data

(60) Provisional application No. 61/915,635, filed on Dec. 13, 2013.

(51) Int. Cl.
  *A61B 17/70* (2006.01)
  *A61B 90/30* (2016.01)

(52) U.S. Cl.
  CPC .......... *A61B 17/7079* (2013.01); *A61B 90/30* (2016.02); *A61B 2017/00526* (2013.01); *A61B 2017/0256* (2013.01); *A61B 2090/306* (2016.02)

(56) References Cited

U.S. PATENT DOCUMENTS

| | | | |
|---|---|---|---|
| 4,409,968 A | 10/1983 | Drummond | |
| 4,411,259 A | 10/1983 | Drummond | |
| 4,733,657 A | 3/1988 | Kluger | |
| 4,957,495 A | 9/1990 | Kluger | |
| 5,010,879 A | 4/1991 | Moriya et al. | |
| 5,059,194 A | 10/1991 | Michelson | |
| 5,167,662 A | 12/1992 | Hayes et al. | |
| 5,219,349 A | 6/1993 | Krag et al. | |
| 5,242,443 A | 9/1993 | Kambin | |
| 5,281,223 A | 1/1994 | Ray | |
| 5,385,565 A | 1/1995 | Ray | |
| 5,478,340 A | 12/1995 | Kluger | |
| 5,487,743 A | 1/1996 | Laurain et al. | |
| 5,591,167 A | 1/1997 | Laurain et al. | |
| 5,728,046 A | 3/1998 | Mayer et al. | |
| 5,846,193 A | 12/1998 | Wright | |
| RE36,221 E | 6/1999 | Breard et al. | |
| 5,928,139 A | 7/1999 | Koros et al. | |
| 5,944,658 A | 8/1999 | Koros et al. | |
| 6,074,391 A | 6/2000 | Metz-Stavenhagen et al. | |
| 6,083,154 A | 7/2000 | Liu et al. | |
| 6,090,113 A | 7/2000 | Le Couedic et al. | |
| 6,123,707 A | 9/2000 | Wagner | |
| 6,139,493 A | 10/2000 | Koros et al. | |
| 6,146,386 A | 11/2000 | Blackman et al. | |
| 6,485,518 B1 | 11/2002 | Cornwall et al. | |
| 6,506,151 B2 | 1/2003 | Estes et al. | |
| 6,530,929 B1 | 3/2003 | Justis et al. | |
| 6,616,666 B1 | 9/2003 | Michelson | |
| 6,616,667 B1 | 9/2003 | Steiger et al. | |
| 6,712,818 B1 | 3/2004 | Michelson | |
| 7,008,422 B2 | 3/2006 | Foley et al. | |
| 7,011,660 B2 | 3/2006 | Sherman et al. | |
| 7,188,626 B2 | 3/2007 | Foley et al. | |
| 7,250,052 B2 | 7/2007 | Landry et al. | |
| 7,578,822 B2 | 8/2009 | Rezach et al. | |
| 7,621,918 B2 | 11/2009 | Jackson | |
| 7,666,188 B2 | 2/2010 | Anderson et al. | |
| 7,867,259 B2 | 1/2011 | Foley et al. | |
| 7,914,536 B2 | 3/2011 | MacDonald et al. | |
| 7,922,727 B2 | 4/2011 | Songer et al. | |
| 7,955,355 B2 | 6/2011 | Chin | |
| 7,988,713 B2 | 8/2011 | Metz-Stavenhagen | |
| 8,002,798 B2 | 8/2011 | Chin et al. | |
| 8,002,802 B2 | 8/2011 | Abdou | |
| 8,052,720 B2* | 11/2011 | Kuester | A61B 17/7037 606/246 |
| 8,118,737 B2 | 2/2012 | Perez-Cruet et al. | |
| 8,157,809 B2 | 4/2012 | Butters et al. | |
| 8,162,952 B2 | 4/2012 | Cohen et al. | |
| 8,177,817 B2 | 5/2012 | Fallin | |
| 8,197,488 B2 | 6/2012 | Sorrenti et al. | |
| 8,231,635 B2 | 7/2012 | Sharifi-Mehr et al. | |
| 8,287,546 B2 | 10/2012 | King et al. | |
| 8,357,184 B2 | 1/2013 | Woolley et al. | |
| 8,403,940 B2 | 3/2013 | Parker et al. | |
| 8,506,574 B2 | 8/2013 | Butters et al. | |
| 8,523,916 B2 | 9/2013 | Anderson et al. | |
| 8,894,655 B2 | 11/2014 | Fallin et al. | |
| 8,915,925 B2 | 12/2014 | Butters et al. | |
| 9,307,972 B2 | 4/2016 | Lovell et al. | |
| 9,402,661 B2 | 8/2016 | Reitblat et al. | |
| 9,408,716 B1 | 8/2016 | Reitblat et al. | |
| 9,510,875 B2 | 12/2016 | Reitblat et al. | |
| 2003/0055430 A1 | 3/2003 | Kim | |
| 2003/0073998 A1 | 4/2003 | Pagliuca et al. | |
| 2003/0187436 A1 | 10/2003 | Bolger et al. | |
| 2004/0034351 A1 | 2/2004 | Sherman et al. | |
| 2004/0138662 A1 | 7/2004 | Landry et al. | |
| 2004/0143265 A1 | 7/2004 | Landry et al. | |
| 2004/0147928 A1 | 7/2004 | Landry et al. | |
| 2004/0172022 A1 | 9/2004 | Landry et al. | |
| 2004/0215190 A1 | 10/2004 | Nguyen et al. | |
| 2004/0260287 A1 | 12/2004 | Ferree | |
| 2005/0010220 A1 | 1/2005 | Casutt et al. | |
| 2005/0010221 A1 | 1/2005 | Dalton | |
| 2005/0021030 A1 | 1/2005 | Pagliuca et al. | |
| 2005/0021031 A1 | 1/2005 | Foley et al. | |
| 2005/0021040 A1 | 1/2005 | Bertagnoli | |
| 2005/0038436 A1 | 2/2005 | Michelson | |
| 2005/0070917 A1 | 3/2005 | Justis | |
| 2005/0090822 A1 | 4/2005 | DiPoto | |
| 2005/0090833 A1 | 4/2005 | DiPoto | |
| 2005/0131421 A1 | 6/2005 | Anderson et al. | |
| 2005/0131422 A1 | 6/2005 | Anderson et al. | |
| 2005/0154389 A1 | 7/2005 | Selover et al. | |
| 2005/0245928 A1 | 11/2005 | Colleran et al. | |
| 2006/0069391 A1 | 3/2006 | Jackson | |
| 2006/0111714 A1 | 5/2006 | Foley | |
| 2006/0195114 A1 | 8/2006 | Bertagnoli | |
| 2006/0200135 A1 | 9/2006 | Sherman et al. | |
| 2006/0264934 A1 | 11/2006 | Fallin | |
| 2007/0233079 A1 | 10/2007 | Fallin et al. | |
| 2008/0077138 A1 | 3/2008 | Cohen et al. | |
| 2008/0125788 A1 | 5/2008 | Cohen et al. | |
| 2008/0125817 A1* | 5/2008 | Arnett | A61B 17/7002 606/319 |
| 2009/0099605 A1 | 4/2009 | Fallin et al. | |
| 2009/0216327 A1 | 8/2009 | Miller et al. | |
| 2010/0036443 A1 | 2/2010 | Hutton et al. | |
| 2010/0298647 A1 | 11/2010 | Black et al. | |
| 2011/0172494 A1 | 7/2011 | Bass et al. | |
| 2012/0226284 A1 | 9/2012 | Sorrenti et al. | |
| 2012/0296171 A1* | 11/2012 | Lovell | A61B 17/0206 600/213 |
| 2012/0303034 A1* | 11/2012 | Woolley | A61B 17/0206 606/90 |
| 2013/0110113 A1 | 5/2013 | Glazer | |
| 2013/0310942 A1 | 11/2013 | Abdou | |
| 2014/0018860 A1 | 1/2014 | Butters et al. | |
| 2014/0277206 A1 | 9/2014 | Reitblat et al. | |
| 2015/0066088 A1 | 3/2015 | Brinkman et al. | |
| 2015/0088210 A1* | 3/2015 | Reitblat | A61B 17/7076 606/86 A |
| 2015/0164495 A1 | 6/2015 | Petit | |

FOREIGN PATENT DOCUMENTS

| | | |
|---|---|---|
| EP | 0528177 A2 | 2/1993 |
| EP | 0611116 | 8/1994 |
| EP | 665731 | 8/1995 |
| WO | 9409726 | 5/1994 |
| WO | 0141681 A1 | 6/2001 |
| WO | 04021899 | 3/2004 |
| WO | 04037074 | 5/2004 |
| WO | 04041100 | 5/2004 |
| WO | 04080318 A1 | 9/2004 |
| WO | 05018466 | 3/2005 |

(56) References Cited

FOREIGN PATENT DOCUMENTS

| WO | 05023123 | 3/2005 |
|---|---|---|
| WO | 05032358 | 4/2005 |
| WO | 05060534 A | 7/2005 |
| WO | 2006060430 | 6/2006 |
| WO | 2007092056 | 8/2007 |
| WO | 2010121291 | 10/2010 |
| WO | 2010135537 A2 | 11/2010 |
| WO | 2013178940 A1 | 12/2013 |

OTHER PUBLICATIONS

Diapason, Surgical Texchnique Catalog, Diapasan Spinal System, Jan. 2002.
Extended European Search Report for Application No. 14197996.3 dated Jun. 29, 2015.
Kambin et al, "Percutaneous Posterolateral Lumbar Discectomy and Decompression with a 6.9-millimeter cannula", The Journal of Bone and Joint Surgery, pp. 822-831, Jul. 1991.
Kambin, Minimally Invasive Techniques in Spinal Surgery Current Practice, Neurosurgical Focus, wwwspineuniversecom, 16 pages, printed Aug. 24, 2005.
Leu et al., Percutaneous Fusion of the Lumbar Spine, State of the Art Reviews, vol. 6, No. 3, pp. 593-604, Sep. 1992.
Pathfinder; Minimally Invasive Pedicie Fixation System. Spinal Concepts Product Brochure p. 1-4, May 2003.
Prybis, U.S. Appl. No. 61/515,443, filed Aug. 5, 2011.
Reitblat et al., U.S. Appl. No. 14/034,021, filed Sep. 23, 2013.
Reitblat et al., U.S. Appl. No. 14/099,159, filed Dec. 6, 2013.
Reitblat et al., U.S. Appl. No. 61/783,098, filed Mar. 14, 2013.
Engineering drawing of parallel post distractor (discussed in accompanying letter).

* cited by examiner

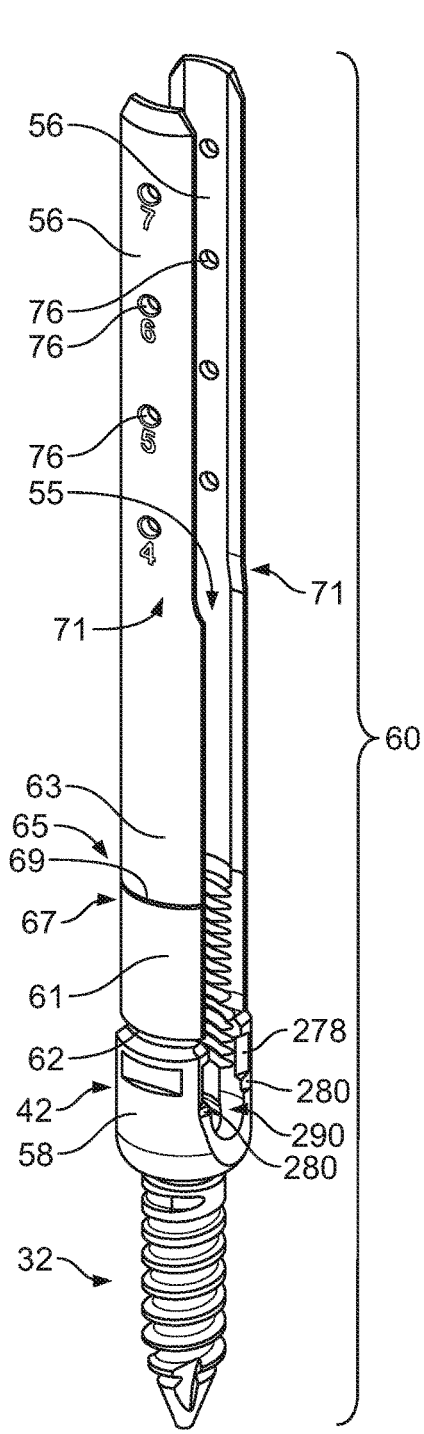
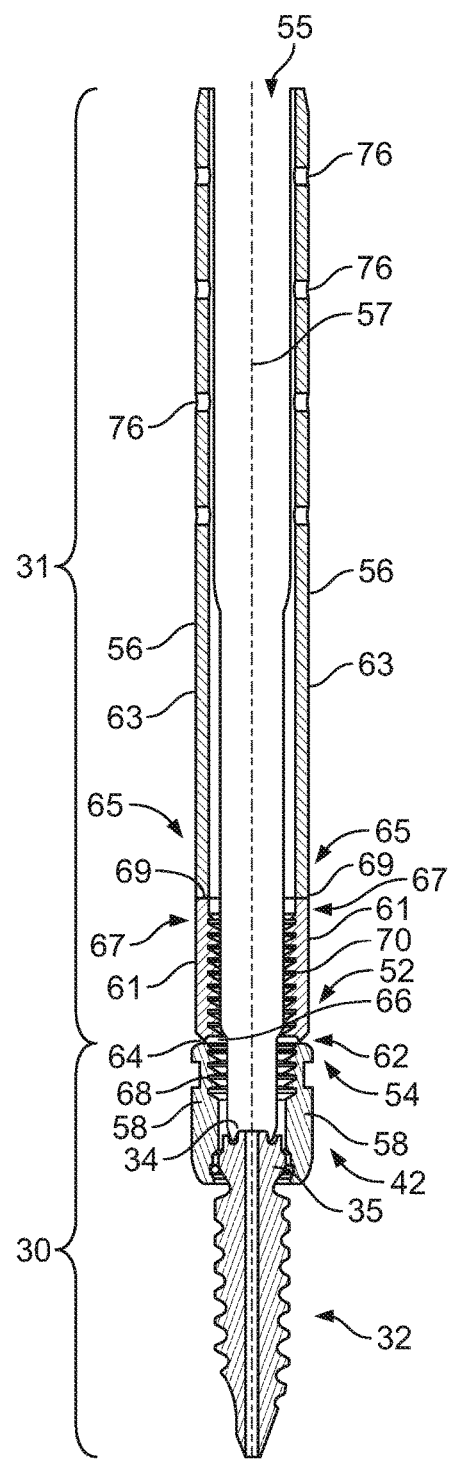
FIG. 2A
FIG. 2B

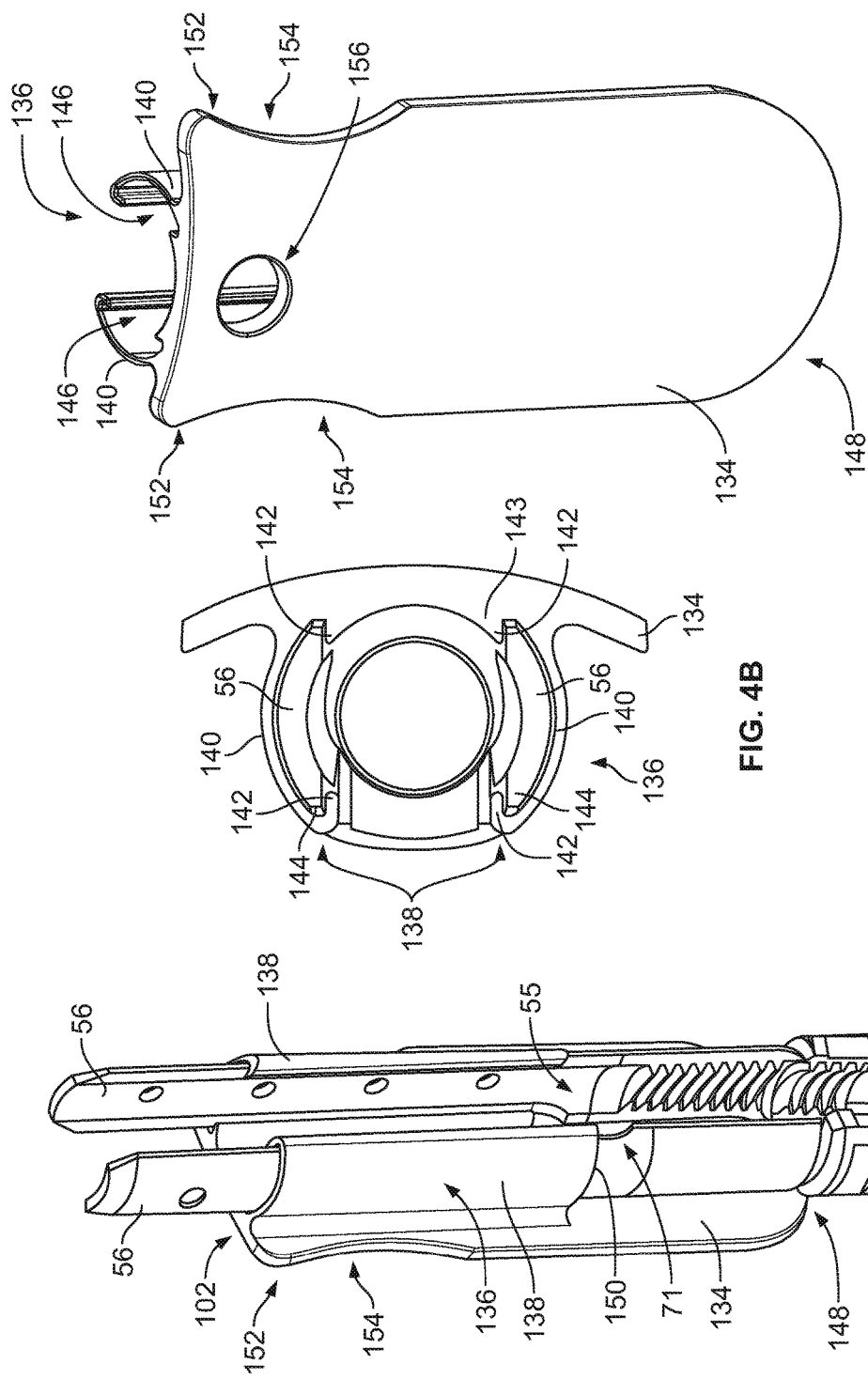

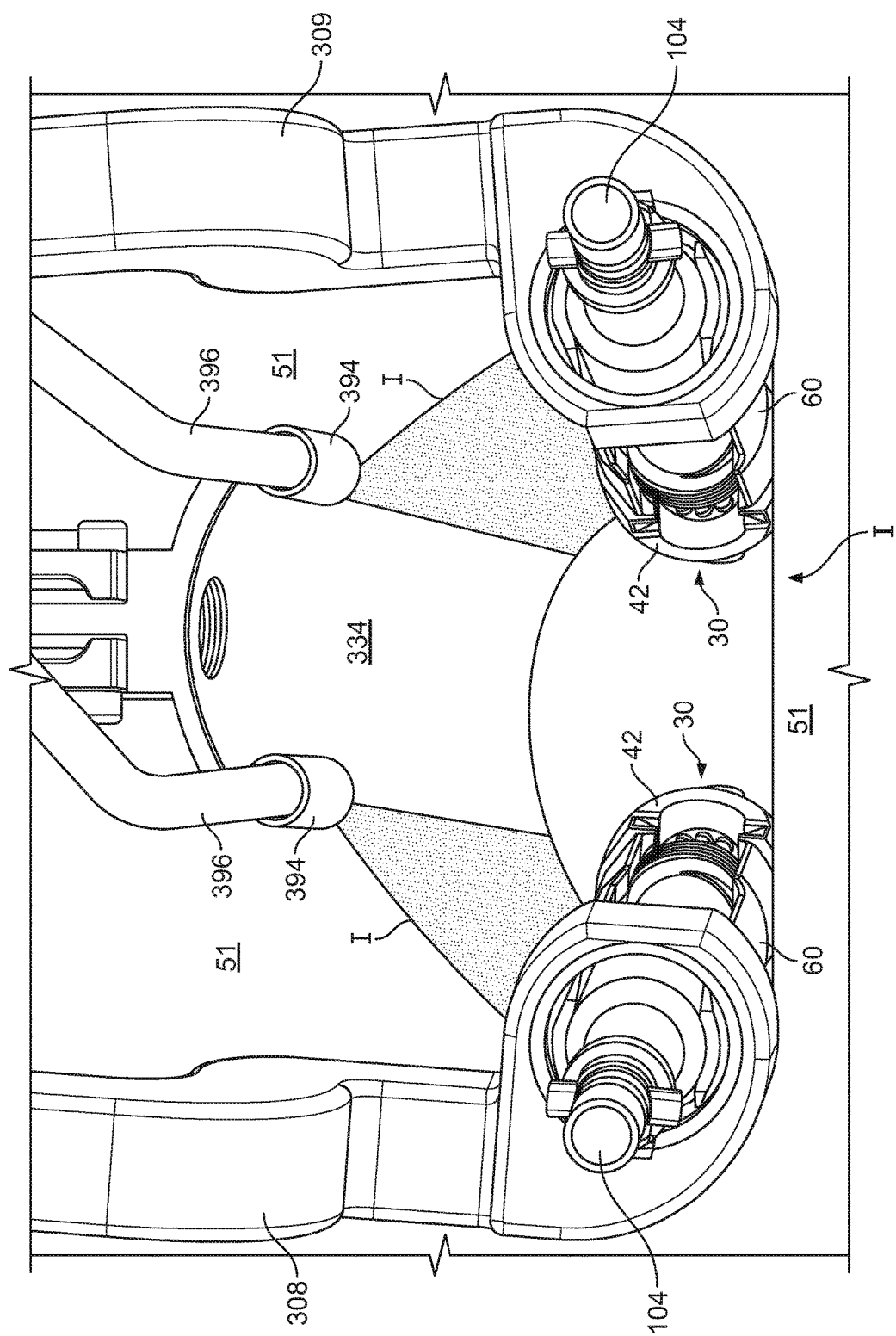

TISSUE RETRACTION AND VERTEBRAL DISPLACEMENT DEVICES, SYSTEMS, AND METHODS FOR POSTERIOR SPINAL FUSION

CROSS-REFERENCE TO RELATED APPLICATIONS

This application is a divisional of U.S. application Ser. No. 14/569,013, filed on Dec. 12, 2014, which claims the benefit of the filing date of U.S. Provisional Patent Application No. 61/915,635 filed Dec. 13, 2013, the disclosures of which are hereby incorporated herein by reference.

BACKGROUND OF THE INVENTION

The present invention relates to devices, systems, and methods in connection with posterior spinal fusion.

Pedicle screw fixation constructs have been in use for decades in conjunction with spinal fusion procedures, in which adjacent vertebral segments are fused to improve spinal stability or correct certain spinal deformities. Older approaches for inserting these pedicle screw fixation constructs involved open procedures, in which relatively large skin incisions were created to expose a substantial portion of the patient's spinal column, in order to allow for insertion of the pedicle screws and manipulation of spinal rods through openings adjacent to the heads of the screws.

Over time, less invasive approaches have been developed. Typically, in such approaches, pedicle screws are inserted into the pedicles of the same or adjacent vertebrae of a patient's spine through individual percutaneous incisions corresponding to the pedicle screws. Fixation or fusion rods are then inserted into the body through one of those incisions, or through an additional incision adjacent to the most cephalad or caudal pedicle screw, and the rod is rigidly connected to the pedicle screws such that the rod extends along the longitudinal axis of the spine (i.e., along the cephalad/caudal direction) in order to fix the relative positions of the adjacent vertebrae to which the rod is connected. In some such minimally invasive procedures, a device (e.g., a cannula, tower, or portal) is connected to each of the pedicle screws and extends through the respective percutaneous incision. Moreover, it is known to utilize separate elongate blades connected with the screws. Such devices provide a percutaneous passageway through the tissue from each incision to the respective pedicle screw, in order to aid in the insertion of a spinal rod. Examples of such passageway devices are described in commonly-assigned U.S. Pat. No. 7,955,355 ("the '355 patent") and U.S. Pat. No. 8,002,798 ("the '798 patent"), the entireties of which are hereby incorporated by reference herein as if fully set forth herein.

Often pedicle screw fixation constructs are used in conjunction with an interbody fusion technique, where the fixation constructs provide additional stability to the interbody fusion. Examples of interbody fusion techniques performed along a posterior approach include posterior lumbar interbody fusion (PLIF) and transforaminal lumbar interbody fusion (TLIF). Examples of interbody fusion techniques along other approaches to the spine include anterior lumbar interbody fusion (ALIF) and lateral interbody fusion. Typically, all of such interbody fusion techniques involve removing at least a portion of the intervertebral disc between two adjacent vertebral bodies and then positioning an interbody implant (such as a cage, which may be packed with bone graft material) into the intervertebral space created by the removal of the disc material.

Although considerable effort has been devoted in the art to optimization of such spinal fusion systems and techniques, still further improvement would be desirable.

BRIEF SUMMARY OF THE INVENTION

One aspect of the present invention provides a retractor device for engaging a connecting element affixed to a vertebra of a spine. The connecting element preferably has a passageway device connected thereto and extending proximally therefrom along a longitudinal axis. The passageway device preferably has at least one longitudinal opening extending along at least a portion of its longitudinal axis. The retractor device according to this aspect of the invention desirably includes an engagement portion and a retractor blade connected to the engagement portion. The engagement portion is desirably adapted to receive at least a portion of the passageway device therein such that the retractor blade is positioned so as to cover at least a portion of the longitudinal opening of the passageway device.

According to one aspect of the invention, the width of the retractor blade is wider than the width of the passageway device. According to another aspect of the invention, the engagement portion extends along the passageway device to the connecting element. According to a further aspect of the invention, a distal end of the engagement portion is adapted to securely engage the connecting element. According to yet a further aspect of the invention, a proximal end of the retractor device includes a connector for engagement by a manipulation device. According to another aspect of the invention, the passageway device includes a first blade and a second blade, and the engagement portion includes a first blade receiver and a second blade receiver adapted to receive the respective first and second blades therein. According to a further aspect of the invention, an exterior of the engagement portion defines a second longitudinal opening between the first and second blade receivers.

Further aspects of the invention provide a retraction system including a retractor device and a passageway device having first and second blades. According to a further aspect of the invention, at least one of the first and second blades has a step where the width of the blade changes, and a distal end of the engagement portion of the retractor device is engageable with that step.

According to an additional aspect of the invention, the distal end of the retractor blade is positionable proximate a proximal end of the connecting element. According to another aspect of the invention, the distal end of the retractor blade is rounded. According to yet another aspect of the invention, the distal end of the retractor blade includes a slot alignable with an opening in the connecting element. According to an additional aspect of the invention, a proximal portion of the retractor device includes at least one gripping portion shaped to be gripped by hand. According to another aspect of the invention, the retractor blade has an arcuate shape. According to yet another aspect of the invention, the retractor blade of the retractor device is longer than the engagement portion.

Yet further aspects of the invention provide a retraction system including first and second retractor devices and first and second shafts. The first and second shafts are receivable within the respective passageway devices such that a distal portion of each of the shafts is positioned proximate the respective connecting element and a proximal portion of each of the shafts is engageable by a manipulation device. The first and second shafts are desirably adapted to transfer a sufficient force to the respective connecting elements to displace the vertebrae with respect to one another in response to relative displacement of the first and second shafts induced by the manipulation device.

According to an aspect of the invention, the distal portion of the first shaft includes a threaded portion engageable with threads in the connecting element or the passageway device. According to another aspect of the invention, the retraction system further includes the manipulation device.

Further aspects of the invention provide a retraction system including a plurality of retractor devices having retractor blades of different longitudinal lengths. According to this aspect of the invention, the retraction system may further include a plurality of shafts receivable within a respective one of the passageway devices such that a distal portion of each one of the plurality of shafts is positioned proximate the respective connecting element and a proximal portion of each one of the plurality of shafts is engageable by a manipulation device. At least one of the shafts may include a plurality of markings, each of which corresponds to a longitudinal length of one of the retractor devices.

Yet further aspects of the invention provide a method of displacing tissue within a body. The method according to this aspect of the invention desirably includes connecting first and second connecting elements to respective first and second vertebrae of a spine within the body, the first and second connecting elements each having a respective first and second passageway device connected thereto and extending proximally therefrom, and the method also desirably includes positioning first and second retractor blades along at least a portion of respective longitudinal openings extending along at least a portion of the longitudinal axes of the respective first and second passageway devices.

According to an aspect of the invention, the steps of positioning the retractor blades include coupling the retractor blades with the respective passageway devices. According to a further aspect of the invention, coupling the retractor blades with the passageway devices includes receiving at least a portion of each of the passageway devices with a respective engagement portion connected to each of the respective blades. According to another aspect of the invention, the method further includes forming an opening in skin of the body extending between the first and second passageway devices. According to a further aspect of the invention, the method further includes enlarging the opening with an intermediate retractor blade positioned between the first and second passageway devices. According to another aspect of the invention, the method includes inserting an interbody implant through the opening and into an intervertebral space between the first and second vertebrae. According to a further aspect of the invention, the method further includes moving at least a portion of a spinal fusion rod within at least one of the first and second passageway devices, and securing the spinal fusion rod to the first and second connecting elements.

Yet further aspects of the invention provide a method of displacing vertebral bodies. The method according to this aspect of the invention desirably includes securing a distal end of each of a first extender and a second extender within a respective first and second cage of a respective first and second connecting element affixed to a respective first and second vertebra of a spine, and the method also desirably includes displacing the first extender with respect to the second extender to displace the first and second vertebrae with respect to one another.

According to an aspect of the invention, the connecting elements include pedicle screws. According to a further aspect of the invention, the cages are polyaxially coupled to the respective pedicle screws. According to yet a further aspect of the invention, the steps of securing the distal ends of the extenders within the cages lock polyaxial movement of the cages with respect to the respective pedicle screws.

According to another aspect of the invention, the extenders each include a shaft. According to a further aspect of the invention, the connecting elements each have a respective passageway device connected thereto and extending proximally therefrom. According to this aspect of the invention, securing the distal ends of the extenders within the cages includes securing a distal portion of each of the shafts within the respective cage such that the shafts extend within and along the longitudinal axes of the respective passageway devices. According to another aspect of the invention, securing the distal ends of the extenders within the cages includes securing each shaft within the respective cage with a respective set screw such that the shafts each extend transverse to the longitudinal axis of the respective extender. According to a further aspect of the invention, the extenders are each integrally formed with a respective retractor blade.

Yet further aspects of the invention provide a system for displacing vertebral bodies. The system according to this aspect of the invention desirably includes a first extender, a second extender, and a manipulation device. The distal ends of each of the first and second extenders are preferably configured to be securely engaged within a respective first and second cage of a respective first and second connecting element affixable to a respective first and second vertebra of the spine. The manipulation device is preferably engageable with the first and second extenders such that the manipulation device is configured to displace the first and second vertebrae with respect to one another by inducing movement of the first extender with respect to the second extender when the first and second extenders are securely engaged with the first and second connecting elements when affixed to the spine.

According to an aspect of the invention, the extenders each include a shaft, at least a portion of which is configured to be securely engaged within the respective cage. According to a further aspect of the invention, each of the connecting elements have a respective passageway device connected thereto and extending proximally therefrom. According to this aspect of the invention, the shafts are each receivable within and along the longitudinal axis of a respective passageway device. According to yet a further aspect of the invention, a distal portion of at least one of the shafts includes a threaded portion engageable with threads in the one of the connecting elements or the associated passageway device. According to another aspect of the invention, the shafts each extend transverse to a longitudinal axis of the associated extender, and the shafts are each configured to be securely engaged within the respective cage by a respective set screw. According to a further aspect of the invention, the extenders are each integrally formed with a respective retractor blade.

BRIEF DESCRIPTION OF THE DRAWINGS

FIG. 2A is a perspective view of a blade-screw of FIG. 1.

FIG. 2B is a sectional view of the blade-screw of FIG. 2A.

FIG. 4A is a perspective view of a retraction blade engaged with a portion of a blade-screw, in accordance with the embodiment of FIG. 3A.

FIG. 4B is a plan view of the arrangement of FIG. 4A.

FIG. 4C is a perspective view of a retraction blade, in accordance with the embodiment of FIG. 3A.

FIG. 11B is a perspective view of the assembly of FIG. 11A positioned in an incision in a patient.

DETAILED DESCRIPTION

Where reference is made herein to directional terms such as "proximal," "proximal most," "distal," and "distal most," it is to be understood that "proximal" and "proximal most" refer to locations closer to a user or operator of the device or method being described and that "distal" and "distal most" refer to locations further from a user or operator of the device or method being described.

Figure 1:
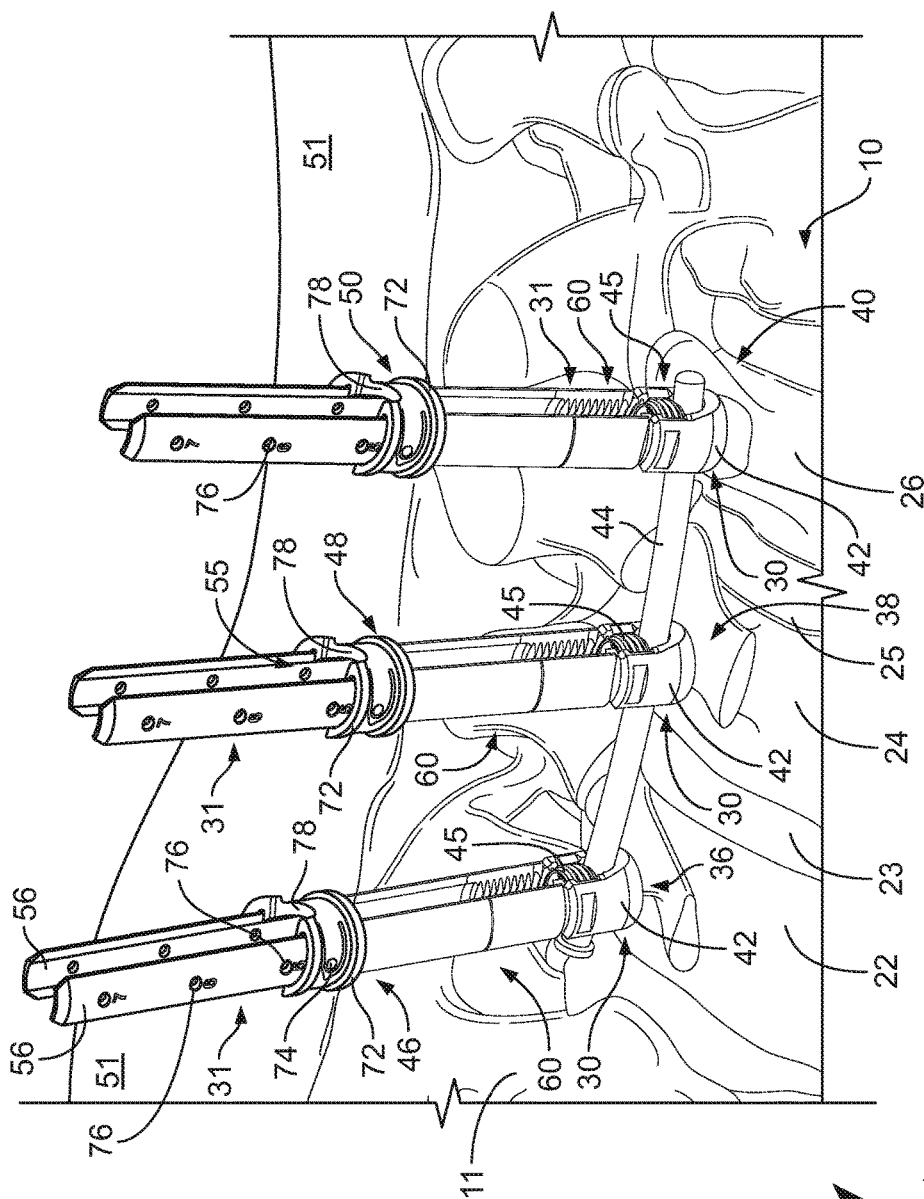
FIG. 1 is a perspective view of a system of blade-screws connected to a spine, in accordance with an embodiment of the present invention.

FIG. 1 illustrates a system of connecting elements 30, passageway devices 31, and a spinal fusion element or rod 44 connected to a spine 10. The spine 10 has a cephalad direction 12, a caudal direction 14, an anterior direction 16, a posterior direction 18, and a medial/lateral axis 20, all of which are oriented as shown by the arrows bearing the same reference numerals. In this application, "left" and "right" are used with reference to a posterior view, i.e., a view from behind the spine 10. "Medial" refers to a position or orientation toward a sagittal plane (i.e., plane of symmetry that separates left and right sides from each other) of the spine 10, and "lateral" refers to a position or orientation relatively further from the sagittal plane.

As shown in FIG. 1, the spine 10 includes a first vertebra 22, a second vertebra 24, and a third vertebra 26. Between the first and second vertebrae 22, 24 is a first intervertebral disc 23, and between the second and third vertebrae 24, 26 is a second intervertebral disc 25. The systems and methods herein may be applicable to any vertebra or vertebrae of the spine 10 and/or the sacrum 11. As such, the term "vertebrae" may be broadly interpreted to include all vertebrae, as well as the sacrum. As shown in the figure, the connecting elements 30 and associated passageway devices 31 are connected to respective pedicles 36, 38, 40 on the right side of the respective first, second, and third vertebrae 22, 24, 26. Although the system illustrated in FIG. 1 spans three vertebrae, other embodiments of systems in accordance with the present invention may span fewer or more vertebrae. For example, additional connecting elements 30 and passageway devices 31 may be connected to additional vertebrae along the spine 10. Other embodiments of systems in accordance with the present invention may include multiple systems of connecting elements 30, passageway devices 31, and spinal fusion rods 44, each of which may span any number of vertebrae. In some such embodiments, systems of connecting elements 30, passageway devices 31, and spinal fusion rods 44 may be positioned on both sides of the spinous processes along the spine (i.e., on both the left and right sides of the spine).

The connecting elements 30 each include an anchoring element or screw 32 (see FIGS. 2A-B) implanted in the respective pedicles 36, 38, 40 and a coupling element or cage 42 for receiving the spinal fusion rod 44 therein. The cages 42 may be coupled to the respective screws 32 in various ways known in the art. For example, as shown in FIG. 2B, the cages 42 and the screws 32 may be polyaxially coupled. In other embodiments (not shown), the coupling between the cages 42 and the screws 32 may be a monoaxial coupling or a uniplanar coupling, or the cages 42 may be rigidly fixed to (e.g., integrally formed with) the screws 32. Each connecting element 30 may also include a set screw 45 for securing the rod 44 within the cage 42. The connecting elements 30 may have the same or similar structure as the connecting elements described in the '798 patent. Alternatively, the connecting elements 30 may have the same or similar structure as the pedicle screws described in U.S. Pat. No. 7,988,713 ("the '713 patent") or the pedicle screws, pedicle hooks, or lamina hooks described in U.S. Pat. No. 6,074,391 ("the '391 patent"). The entire disclosures of the '713 patent and the '391 patent are hereby incorporated by reference herein as if fully set forth herein. Although the anchoring elements are illustrated herein as screws 32, it is to be understood that other types of anchoring elements capable of being secured to vertebral bone may be used, such as the above-referenced hooks described in the '391 patent. Moreover, although the spinal fusion element 44 is illustrated herein as a rod 44, it is to be understood that other types of elements capable of securing together adjacent vertebrae may be used, such as plates, wires, rods, or articulating versions thereof.

The connecting elements 30 may be percutaneously inserted in the body in the same manner as described in the '798 patent. That is, each of the connecting elements 30 may be inserted along a respective guide wire through a separate incision 46, 48, 50 in the skin 51. Sequential dilators may be used to enlarge the passageway between the incisions 46, 48, 50 and the respective pedicles 36, 38, 40. The screws 32 of the connecting elements 30 may be implanted in previously tapped bores in the associated pedicles, or the screws 32 may self-tap into the pedicles. The advancement of each screw 32 into a pedicle may be driven by a driver (not shown) having a distal end engaged with a driver interface 34 on the head 35 of the screw 32 (see FIG. 2B), such that a shaft of the driver extends proximally within the passageway device 31. The driver interface 34 of the head 35 may take the form of that disclosed in U.S. Pat. No. 8,231,635 ("the '635 patent"), the entire disclosure of which is hereby incorporated by reference herein as if fully set forth herein, and the driver may take the form of any one of the screwdrivers disclosed in that patent. The driver may be a powered or a manually operated driver. Additionally, before the connecting elements 30 are inserted into the body, spinal navigation software and/or robotics may be used to help locate the appropriate pedicles 36, 38, 40 and to implant or help guide the implantation of the connecting elements 30 into the pedicles.

The passageway devices 31 are connected to the connecting elements 30 such that the passageway devices 31 extend proximally from the connecting elements 30 though the respective incisions 46, 48, 50. In particular, as shown in FIGS. 2A-B, the distal ends 52 of the passageway devices 31 are connected to the proximal ends 54 of the cages 42. The passageway devices 31 each provide a passageway 55 extending along an axis 57 from the incision 46, 48, 50 to the respective connecting element 30 to aid the percutaneous insertion of the rod 44. The axis 57 (and the associated passageway device 31) may be straight, as illustrated in the figures herein, or the passageway device 31 may define an angled or curved longitudinal axis, as disclosed in certain embodiments of U.S. patent application Ser. No. 14/034,021 ("the '021 application"), filed on Sep. 23, 2013 and entitled "Lumbar-Sacral Screw Insertion and Manipulation," the entire disclosure of which is hereby incorporated by reference herein as if fully set forth herein. Each passageway device 31 may take the form of two blades 56 attached to opposing arms 58 of the associated cage 42. The blades 56 may be separately formed from and detachably connectible to the cages 42, as described in the '798 patent. Alternatively, the blades 56 may be formed as a single piece with the associated cages 42, as also described in the '798 patent. For example, FIGS. 1-2B illustrate an embodiment in which the blades 56 are integrally connected to the associated cages 42 to form monolithic blade-screws 60. In such an embodiment, the blades 56 may be connected to the cages 42 by frangible portions 62. Each frangible portion 62 may include a reduced thickness portion, which may be defined by grooves formed in either or both of the interior and exterior surfaces of the blade-screws 60 at the junction between the blades 56 and the respective arms 58 of the cages 42. In the embodiment illustrated in FIG. 2B, the frangible portions 62 are defined by a groove 64 along the exterior of the blade-screw 60 and a groove 66 along the interior of the blade-screw 60 that is aligned with the exterior groove 64. The frangible portions 62 provide a location for the blades 56 to be broken away from the cages 42 when desired.

The interior of each cage 42 may include threads 68 along the arms 58, and the passageway device 31 may include reduction threads 70 at least along the distal end 52 thereof. In other embodiments (not shown), the reduction threads 70 of the passageway device 31 may not be present while the threads 68 of the cage 42 are present. The set screw 45 is an externally threaded component structured to engage the reduction threads 70 of the passageway device 31 and the threads 68 of the cage 42. Both threads 68 and 70 are aligned such that the set screw 45 can be rotatably advanced distally along the reduction threads 70 of the passageway device 31, after which continued rotation of the set screw 45 will cause the set screw 45 to engage and advance along the threads 68 of the cage 42.

The threads 68 and/or the reduction threads 70 may have a tooth shape as disclosed in the '391 patent. That is, as disclosed in the '391 patent, and as illustrated in FIG. 2B herein, the flank of each thread facing in the distal direction (i.e., towards the screw 32) may be steep and, preferably, is generally horizontal, and the flank of each thread facing in the proximal direction (i.e., away from the screw 32) may be angled at about 30° with respect to the horizontal. The threads 106 of the set screw 45 are preferably complementary to the threads 68 and/or the reduction threads 70 (i.e., the steep flank of each thread 106 of the set screw 45 may be aligned oppositely to the steep flanks of the threads 68, 70).

As discussed above, the blades 56 of the passageway devices 31 are integrally connected to the cages 42 in the monolithic blade-screws 60. Such blade-screws 60 may be constructed by fabricating each cage 42 with its respective passageway device 31 as one piece. For example, a cage 42 with two blades 56 extending therefrom may be machined out of a single piece of material. In another example, the cage 42 with both blades 56 may be cast or molded as a unitary component. In other embodiments, however, subcomponents of the cage 42 and passageway device 31 may be formed separately and then integrally connected together, such as by welding. For example, the blades 56 and the cages 42 may be separately formed (e.g., by machining, casting, or molding), and the distal ends 52 of two blades 56 defining a passageway device 31 may be connected (e.g., by welding) to the proximal ends 54 of the arms 58 of a cage 42. In the case of welding, the welded regions may form the frangible portions 62. In yet another embodiment, each cage 42 may be integrally formed (e.g., by machining, casting, or molding) with two reduction portions 61 extending proximally from the proximal ends 54 of each of the arms 58 of the cage 42. The reduction portions 61 desirably include the reduction threads 70 of what will become the blades 56. Two blade extensions 63 may be separately formed, and the distal ends 65 of those extensions 63 may be integrally connected (e.g., welded) to the proximal ends 67 of the reduction portions 61 at connection 69. As shown in FIGS. 2A-B, each blade extension 63 may have a particular shape or profile that changes along its length. For example, as shown in those figures, the width of each blade 56 may become narrower at one or more steps 71 along its length. The final shape of the blade extensions 63 may be created when the separately formed blade extensions 63 are initially fabricated (e.g., machined, casted, or molded). Alternatively, the blade extensions 63 may initially be formed into larger pieces, which are then further refined to arrive at their final shape. For example, wire-cut electrical discharge machining ("EDM") may be used to modify the shape of the initially formed larger pieces in order to arrive at the final shape of the blade extensions 63. Such modifications (e.g., using wire-cut EDM) may be performed either before or after the blade extensions 63 are integrally connected to the reduction portions 61.

Figure 5:
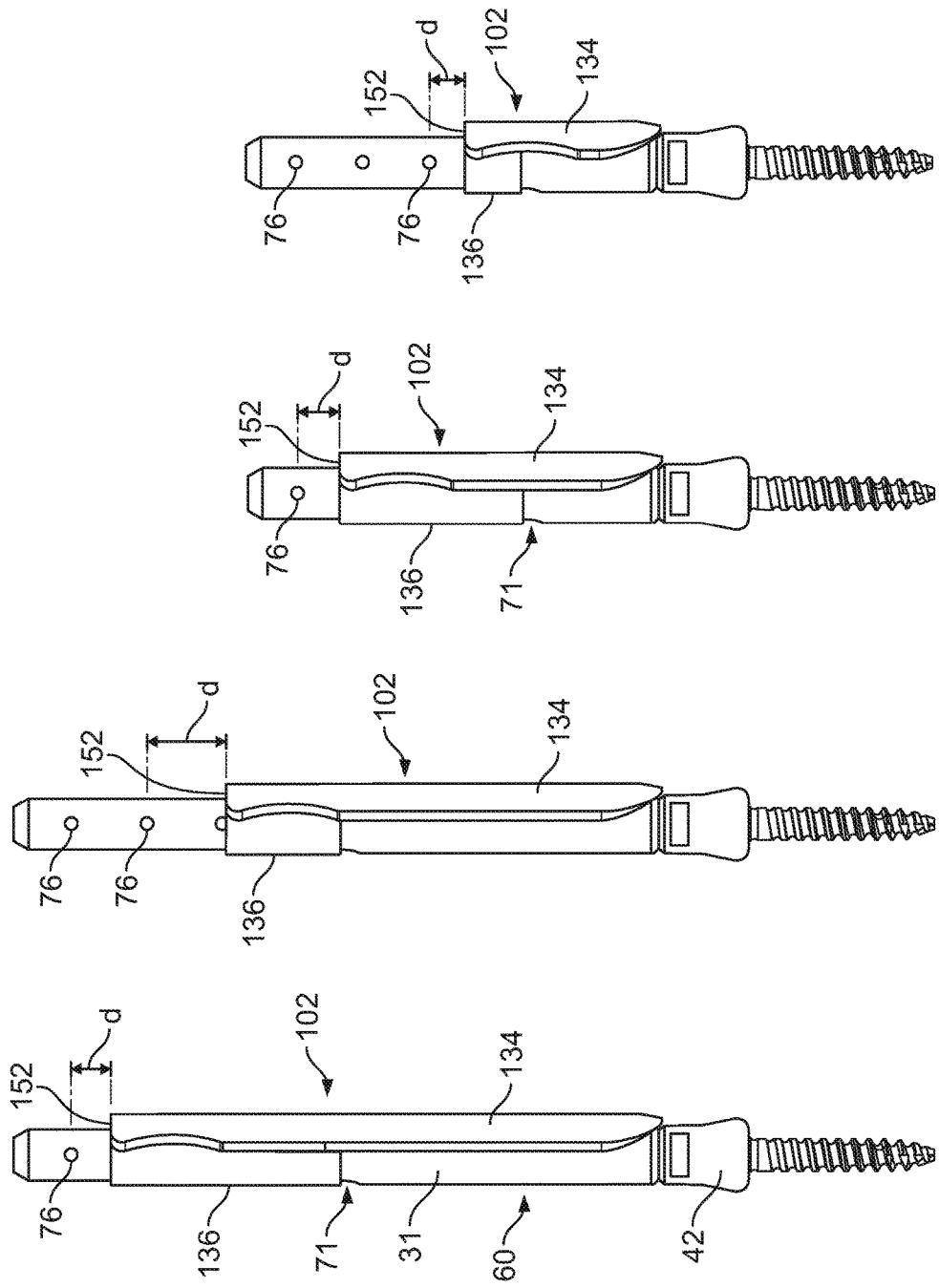
FIG. 5 is a side elevational view of a system of retraction blades engaged with respective blade-screws, in accordance with an embodiment of the present invention.
Figure 6:
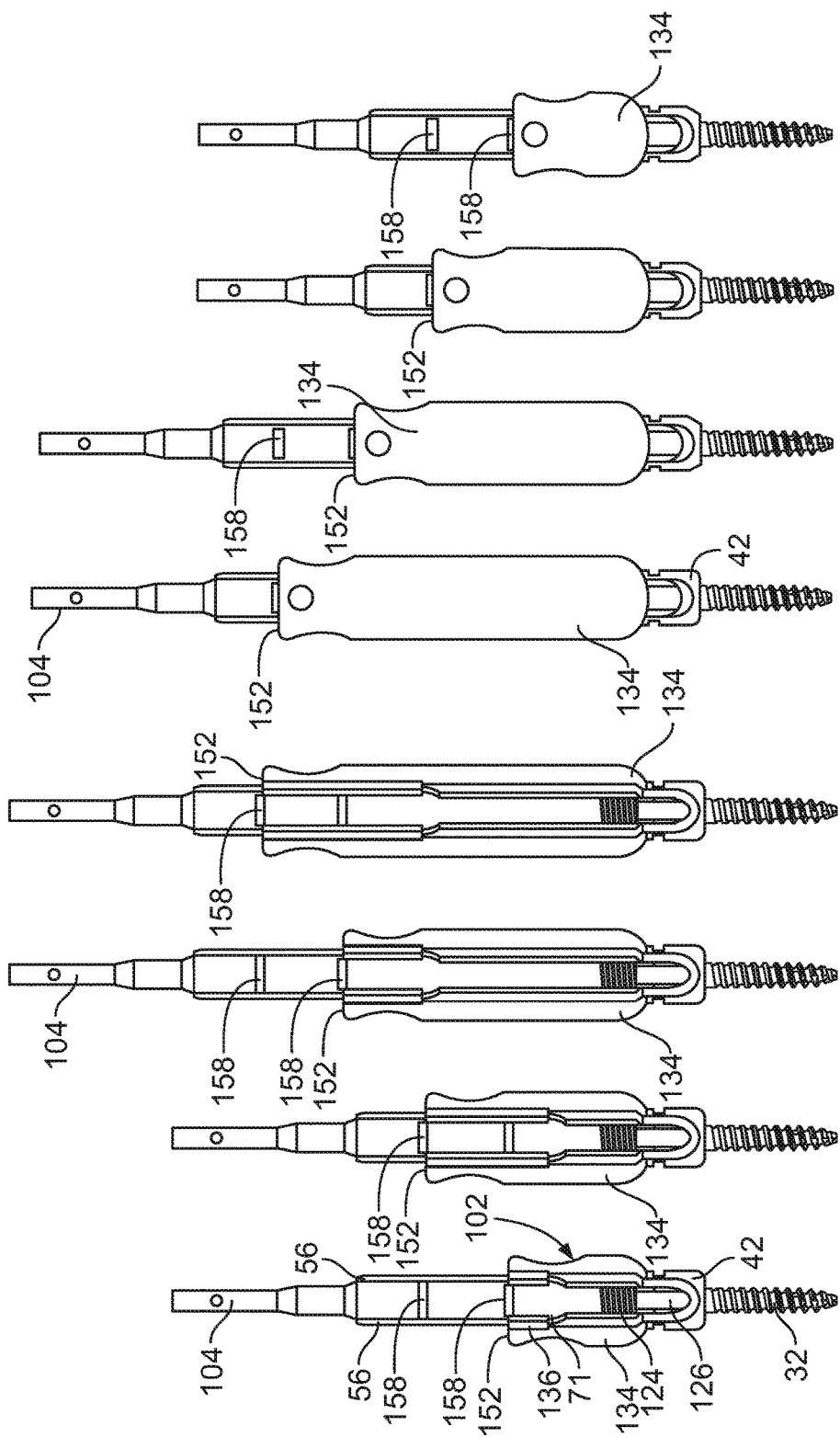
FIG. 6 includes front and rear elevational views of a system of retraction blades and shafts engaged with respective blade-screws, in accordance with an embodiment of the present invention.

In some embodiments, the height of the cages 42 (i.e., the length along longitudinal axis 57) may be about 1.5 cm. The blades 56 may range between about 5 cm long and about 15 cm long. The reduction portions 61 may represent any portion of the length of the blades 56, e.g., about 1 cm to about 4 cm, but may preferably be about 2 cm in length. Systems in accordance with embodiments of the invention may include blade-screws 60 having blades 56 of different lengths, for example, because the distances to be traversed between the skin along a patient's back and the underlying pedicles may be different for different sized patients. For example, such systems may include blades 56 of two different lengths (i.e., long blades and short blades), as shown in FIGS. 5-6. In an exemplary embodiment, the long blades may be about 11 cm long, and the short blades may be about 7 cm long. Although the reduction portions 61 may represent any portion of that length, the reduction portions 61 may have the same length in both the long and short blades. For example, in an embodiment in which the reduction portions are about 2 cm, as discussed above, the blade extensions 64 of the short blades may be about 5 cm long and the blade extensions 64 of the long blades may be about 9 cm long.

Referring to FIG. 1, a coupling 72 may be connected to the blades 56 of each passageway device 31 along the length of the passageway device 31. The couplings 72 may take the form of those disclosed in U.S. Provisional Patent Application No. 61/783,098 ("the '098 application"), filed on Mar. 14, 2013 and entitled "Systems and Methods for Percutaneous Spinal Fusion," the entire disclosure of which is hereby incorporated by reference herein as if fully set forth herein. In other embodiments, the coupling may take the form of the abutment members disclosed in the '798 patent. In addition, the couplings 72 may be connected to the blades 56 in the same manner as disclosed in the '098 application or the '798 patent. For example, as disclosed in the '098 application, the couplings 72 may include flexible tabs 74 having a boss or protuberance (not shown) extending inwardly therefrom for engaging holes 76 along the length of the blades 56. The couplings 72 may also include recesses 78 to provide an extracorporeal template for contouring or selecting the rod 44 to be implanted, as disclosed in the '098 application. Such contouring or selection may also be done in the manner disclosed in commonly owned U.S. Pat. No. 8,177,817 ("the '817 patent") or U.S. Patent Application Publication No. 2007/0233079 ("the '079 Publication"), the entireties of which are hereby incorporated by reference herein as if fully set forth herein.

Once a rod 44 having the desired contour has been selected, it may be inserted into the body and advanced towards the cages 42 of the implanted connecting elements 30, using the passageways 55 through the body tissue provided by the passageway devices 31, until the rod 44 extends between the cages 42. The rod 44 may be secured within the cages 42 by a set screw 45 to thereby stabilize the vertebrae 22, 24, 26 to which the connecting elements 30 are attached. If, after being inserted in the body, the rod 44 is not fully seated in one or more of the cages 42 (e.g., the rod 44 is slightly proud), the rod 44 can be further directed into a particular cage 42 in various ways. For example, the advancement of the set screw 45 distally along the reduction threads 70 of a passageway device 31 and then into the cage 42 may help to push the rod 44 towards and into the cage 42. In addition, or alternatively, a counter torque tube (not shown) can be used to help with the advancement and/or securement of the rod 44 to the cage 42, as disclosed in U.S. patent application Ser. No. 14/099,159 ("the '159 application"), filed on Dec. 6, 2013 and entitled "Compression and Distraction System for Percutaneous Posterior Spinal Fusion," the entire disclosure of which is hereby incorporated by reference herein as if fully set forth herein.

Before final tightening of the set screw 45 in the cage 42, the relative positions of the vertebrae may be adjusted. For example, while the rod 44 is positioned within the cages 42 but before the set screw 45 is tightened to the point that the cages 42 are locked with respect to the rod 44, two or more vertebrae may be moved in the cephalad and caudal directions 12, 14 towards one another (i.e., compression) and/or away from one another (i.e., distraction). One system and method for performing such compression and distraction is disclosed in U.S. Pat. No. 8,157,809 ("the '809 patent"), the entire disclosure of which is hereby incorporated by reference herein as if fully set forth herein. Another such system is disclosed in the '159 application. Other systems and methods for performing compression and distraction are illustrated in FIGS. 3-9 and are discussed herein.

Figure 3A:
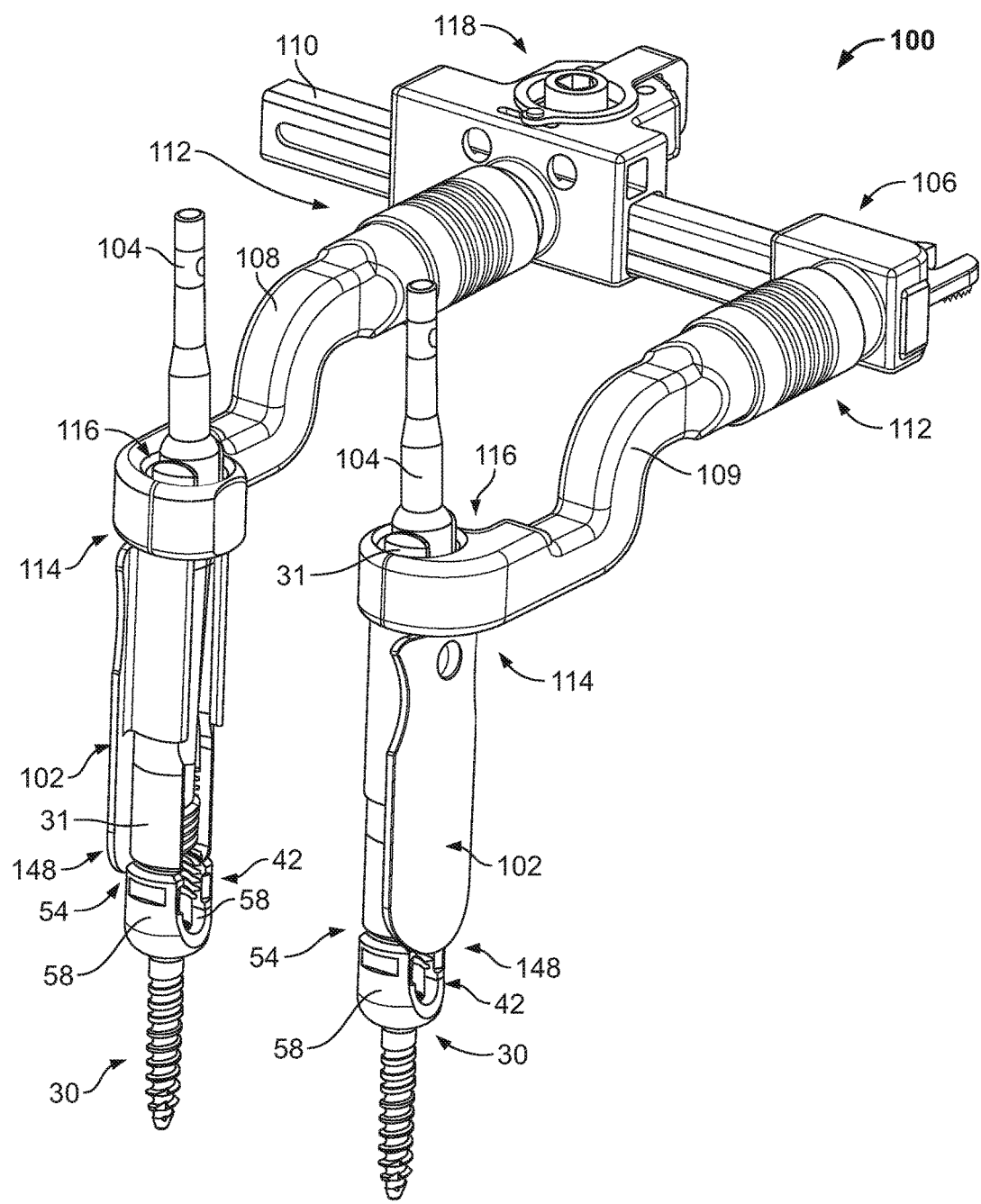
FIG. 3A is a perspective view of a compression/distraction system in engagement with a set of blade-screws, in accordance with an embodiment of the present invention.
Figure 3B:
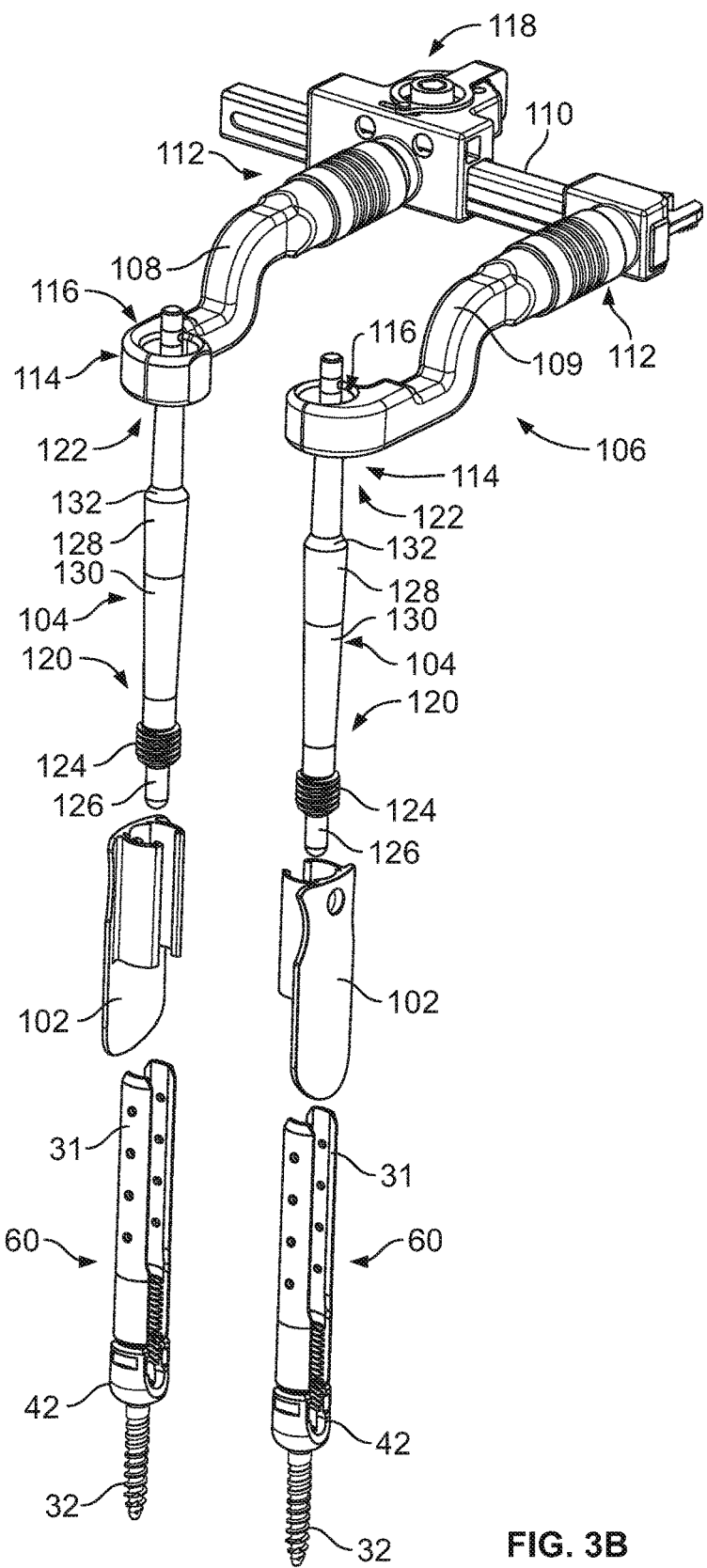
FIG. 3B is a perspective, exploded view of the components of the compression/distraction system and blade-screws illustrated in FIG. 3A.

FIG. 3A discloses a compression/distraction system 100 in accordance with one embodiment of the invention. As shown in the exploded view of FIG. 3B, the system 100 includes a set of retraction blades 102 engageable with respective passageway devices 31 of the blade-screws 60. The system also includes shafts 104 securely engageable with and receivable within the blade-screws 60. The shafts 104 are engageable by a manipulation device 106, which is structured to move the shafts 104 towards and away from one another in order to displace the vertebrae to which the connecting elements 30 are connected. The shafts 104 thus form extenders for transferring displacement forces (e.g., compression and/or distraction forces) from the manipulation device positioned outside the body to the connecting elements 30 connected to vertebrae within the body, to thereby displace the vertebrae with respect to one another. The manipulation device 106 may take any form suitable for engaging the shafts 104 and displacing them relative to one another. In one embodiment, as illustrated in FIGS. 3A-B, the manipulation device 106 includes two arms 108, 109 movably connected to one another by a rack 110. Each arm 108, 109 has a proximal end 112 connected to the rack 110 and a distal end 114 engageable with one of the shafts 104. In one example, the distal ends 114 may each include an opening 116 shaped and sized to securely receive a respective one of the shafts 104 therethrough. As illustrated in FIG. 3A, the openings 116 may each be sized and shaped to securely receive a respective one of the passageway devices 31 therethrough while a shaft 104 is positioned within the passageway device 31. Either or both of the arms 108, 109 may be pivotably connected to the rack 110, which pivoting may be controlled by a respective actuation mechanism (not shown). Moreover, one of the arms 108 may be translationally connected to the rack 110 for movement along the length of the rack 110, while the other arm 109 may have a fixed position at one end of the rack 110. The translating arm 108 may be moved along the rack 110 by actuating a drive mechanism 118, which may rotate a toothed pinion connected to the arm 108 to advance the pinion along corresponding teeth of the rack 110.

The shafts 104 each have a distal portion 120 and a proximal portion 122. The distal portion 120 may be positionable within a respective access device 31 proximate the connecting element 30 and securable, directly or indirectly, to the connecting element 30. As shown in FIG. 3B, the distal portion 120 may include a threaded portion 124 for securing the shaft 104 with respect to the connecting element 30. The threaded portion 124 may engage the threads 68 of the connecting element 30 or it may engage the reduction threads 70 of the passageway device 31, which passageway device 31 is in turn secured to the connecting element 30, as discussed above. The shafts 104 may also be positioned such that the threaded portion 124 extends at least partially along the threads 68 of the connecting element 30 and at least partially along the reduction threads 70 of the passageway device 31. The distal portion 120 of each shaft 104 may also include a distal extension 126 extending distally of the threaded portion 124. The distal extension 126 may be structured such that it engages the head 35 of the screw 32 when the threaded portion 124 is secured to the threads 68 and/or 70. By advancing the threaded portion 124 along the threads 68 and/or 70, the distal extension 126 may forcibly press against the head 35 of the screw 32. This forcible engagement desirably helps to secure the shaft 104 with respect to the connecting element 30. That engagement may also force the head 35 of the screw 32 against the cage 42 within which it is received, which may desirably lock the polyaxial movement of the cage 42 with respect to the screw 32.

Preferably the proximal portion 122 of each shaft 104 includes an engagement portion 128 for engagement by a respective arm 108, 109 of the manipulation device 106. The engagement portion 128 may be shaped and sized to be securely received within the opening 116 of the respective arm 108, 109. For example, the engagement portion 128 may have an outer dimension sized to be closely received within the passageway device 31. The width of the shafts 104 may vary along their lengths, which may beneficially reduce material where not needed. In that regard, the engagement portion 128 may be wider than other portions of the shaft 104, and the shaft may include a tapered portion 130 distally of the engagement portion 128 and another tapered portion 132 proximally of the engagement portion 128.

As shown in FIGS. 4A-C, the retraction blades 102 may each include a blade portion 134 and an engagement portion 136. The engagement portion 136 may be structured to secure the retraction blade 102 to the passageway device 31. In that regard, the engagement portion 136 may include a tubular body having grooves or channels therein for receiving the blades 56 of the passageway device 31, similar to the tubular bodies disclosed in the '159 application. In another example, as shown in FIGS. 4A-C, the engagement portion 136 may include two blade receivers 138 for receiving a respective one of the two blades 56 of a passageway device 31. Each blade receiver 138 may include an outer portion 140 extending around the outside of a blade 56, as shown in the plan view of FIG. 4B, and each blade receiver 138 may include at least one inner extension 142 (e.g., one such inner extension 142 on each side of the blade 56) wrapping around an edge 144 of the blade 56 and along at least a portion of the inside of the blade 56. The inner extension 142 adjacent to the blade portion 134 may be defined by a thicker portion 143 of the blade portion 134, which thicker portion 143 may extend across the space between the blades 56 and define both inner extensions 142 adjacent to the blade portion 134. The space partially surrounded by each blade receiver 138 desirably defines a channel 146 structured to receive a blade 56 of the passageway device 31. The channel 146 may have an arcuate shape along the plane normal to the axis 57 of the passageway device 31, which shape substantially matches the shape of the blades 56 in that plane. The inner extensions 142 desirably constrain the blades 56 to remain in the channels 146.

When the blades 56 are positioned in the channels 146, the blade portion 134 of the retraction blade 102 is preferably positioned alongside the passageway device 31, as shown in FIGS. 3A and 4A, to retract adjacent body tissue. In that regard, the blade portion 134 is preferably wider than the passageway device 31 along a direction transverse to the axis 57 of the passageway device 31, and the blade portion 134 may be arcuate along that width dimension. For example, the blade portion 134 may be about 2 to 3 cm wide, while the passageway device 31 of the blade-screw 60 may be about 1 to 1.5 cm wide. The blade portion 134 also preferably extends along a significant portion of the passageway device 31 positioned beneath the skin 51, so as to keep tissue out of the passageway 55 defined between the blades 56. The distal end 148 of the blade portion 134 is preferably rounded to reduce trauma to the tissue upon insertion of the retraction blade 102 into the body. Preferably the retraction blade 102 is rigid, such that, when the blades 56 are positioned in the channels 146 of the engagement portion 136, the retraction blade 102 stabilizes the blades 56 and prevents them from prematurely disconnecting from the connecting element 30, particularly when the coupling 72 is not positioned on the blades 56.

When the retraction blade 102 is fully positioned on the passageway device 31, the distal end 148 of the blade portion 134 may be positioned proximate the proximal ends 54 of the arms 58 of the cage 42, as shown in FIG. 3A. That position desirably allows a rod 44 positioned between the arms 58 to extend through and beyond the cage 42 without interference from the blade portion 134. In order to come to rest in an appropriate location when the retraction blade 102 is being positioned on the passageway device 31, the retraction blade 102 may be shaped to engage a feature of the passageway device 31. For example, a distal end 150 of the engagement portion 136 may engage the widening step 71 along the blades 56, as shown in FIG. 4A, at which point further distal movement of the retraction blade 102 along the passageway device 31 will be resisted.

To assist with insertion and removal of the retraction blade 102, the proximal end 152 of the blade portion 134 may include cutouts 154 for gripping by hand or by a tool. A hole 156 through the blade portion 134 near the proximal end 150 may also assist with removal of the retraction blade 102 by providing a feature that can be engaged by a tool.

As shown in FIGS. 5-6, a system in accordance with an embodiment of the invention may include blade-screws 60 having blades of two different lengths (i.e., long blades and short blades). The system may also include different length retraction blades 102 for use with differing anatomies. The system may include more types of retraction blade lengths than lengths of blade-screws 60. For example, a system having two lengths of blade-screws 60 may have four lengths of retraction blades 102 (e.g., two retraction blade lengths for use with each blade-screw length), as shown in FIGS. 5-6. In an exemplary embodiment in which the long blades of the blade-screws 60 are about 11 cm long and the short blades of the blade-screws 60 are about 7 cm long, as discussed above, the four lengths of retraction blades 102 may include: a blade portion 134 about 3 to 4 cm long; a blade portion 134 about 5 to 6 cm long; a blade portion 134 about 7 to 8 cm long; and a blade portion 134 about 9-10 cm long. Although only two lengths of blade-screws 60 may be included in the system, the additional lengths of retraction blades 102 may allow for closer tailoring to the specific distance between the skin surface 51 and the implanted connecting element 30. This may be desirable because having the location of the engagement between the shafts 104 and the arms 108, 109 of the manipulation device 106 as close as possible to the underlying pedicles is believed to beneficially reduce the amount of torque applied by the manipulation device 106. Therefore, an appropriate length of retraction blade 102 may be selected by the surgeon or other user so that, when the retraction blade 102 is fully advanced along the passageway device 31, the proximal end 152 of the blade portion 134 may be positioned above the skin surface 51 and as close to the skin as possible. In that way, the engagement between the shafts 104 and the arms 108, 109 of the manipulation device 106, which is located proximally of the proximal end 152 of the blade portion 134, will be above the skin 51 but as close to the underlying connecting element 30 and pedicle as possible.

In order to properly position the different lengths of blade portions 134, each different length retraction blade 102 may have a different length engagement portion 136, as shown in FIGS. 5-6, based on the appropriate distance that the proximal end 152 of the blade portion 134 is to be positioned above the step 71 when the retraction blade 102 is fully advanced along the passageway device 31. In order to assist a surgeon or other user in determining an appropriate length of retraction blade 102, the retraction blades 102 may be identified based on a distance d from the proximal end 152 of the blade portion 134 to one of the holes 76 along the blades 56, as shown in FIG. 5. Additionally, or alternatively, the location of the proximal end 154 of each length blade portion 134 may be indicated by one or more markings 158 (e.g., laser markings) on the shaft 104, as shown in FIG. 6. As shown in FIG. 6, different length shafts 104 may be provided in the system, which blade shaft lengths may correspond to the different lengths of blade-screws 60.

Figure 7:
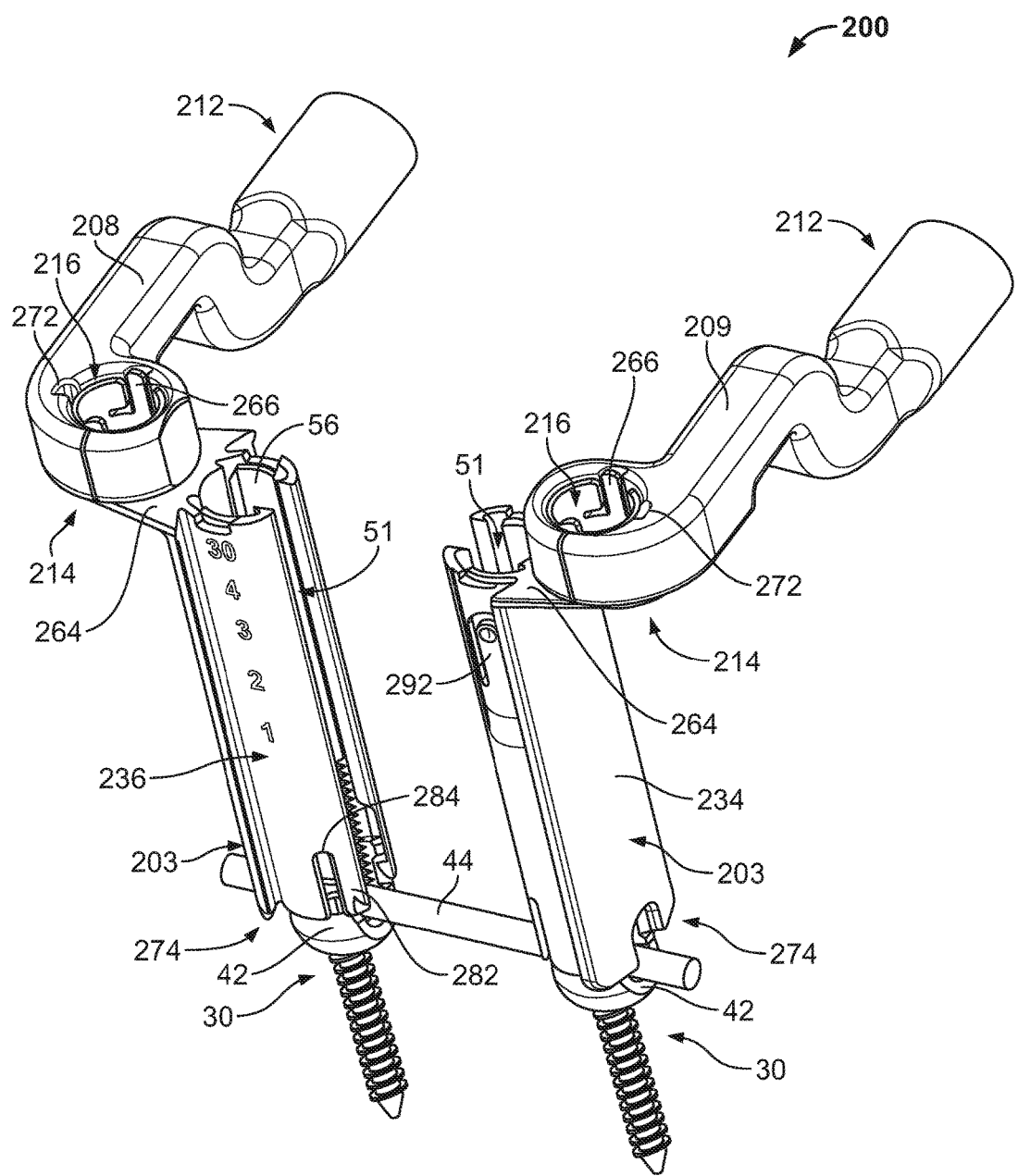
FIG. 7 is a perspective view of a compression/distraction system in engagement with a set of blade-screws, in accordance with another embodiment of the present invention.

FIG. 7 discloses a compression/distraction system 200 in accordance with another embodiment of the invention. The system 200 includes a set of docking members 203 engageable with respective passageway devices 31 and connecting elements 30 of the blade-screws 60, which docking members 203 are also engageable by a manipulation device for moving the docking members 203 towards and away from one another in order to displace the vertebrae to which the connecting elements 30 are connected. The docking members 203 thus form extenders for transferring displacement forces (e.g., compression and/or distraction forces) from the manipulation device positioned outside the body to the connecting elements 30 connected to vertebrae within the body, to thereby displace the vertebrae with respect to one another. The manipulation device may take any form suitable for engaging the docking members 203 and displacing them relative to one another. In one embodiment, the manipulation device may include two arms 208, 209, each having a distal end 214 engageable with one of the docking members 203 and a proximal end 212 connected to a rack (not shown), which may be similar to the rack 110 of the manipulation device 106 illustrated in FIGS. 3A-B. As in the embodiment of the manipulation device 106 illustrated in FIGS. 3A-B, the arms 208, 209 may similarly be pivotably and translationally connected to the rack. The distal ends 214 of the arms 208, 209 may each engage a connector 260 of the respective docking member 203. In one example, the distal ends 214 may each include an opening 216 shaped and sized to securely receive a respective one of the connectors 260 therein.

Figure 8B:
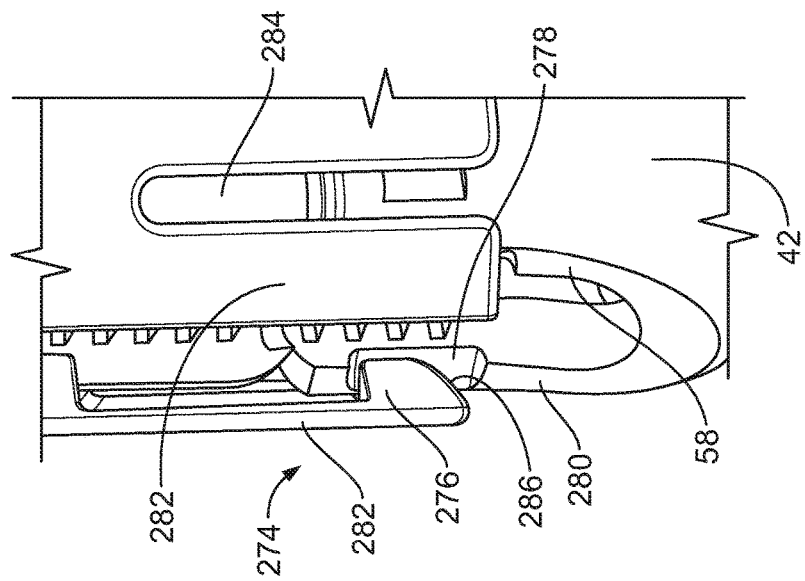
FIG. 8B is a partial, perspective view of a docking member in engagement with a blade-screw, in accordance with the embodiment of FIG. 7.
Figure 8A:
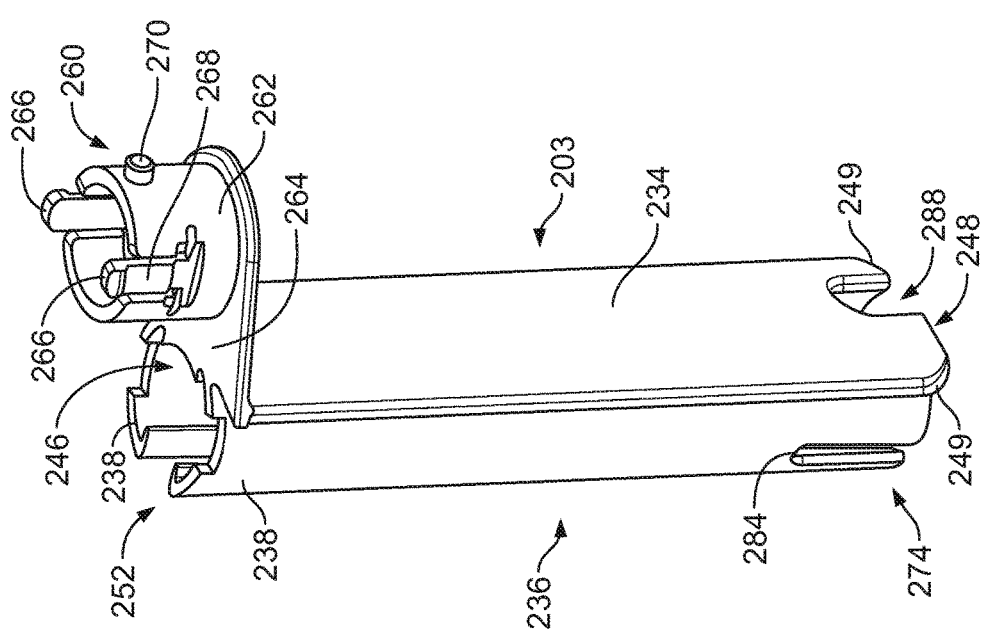
FIG. 8A is a perspective view of a docking member, in accordance with the embodiment of FIG. 7.

Each connector 260 may be structured as a shaft 262 projecting proximally from a lateral extension 264 at the proximal end 252 of the docking member 203. As shown in FIG. 8A, the shaft 262 may be hollow. The shaft 262 may also include at least one (e.g., two) flexible tabs 266, each of which may have an exterior face 268 shaped to securely engage a feature (not shown) in the opening 216 of the respective arm 208, 209. When the arms 208, 209 are connected to the connectors 260, the proximal ends of the tabs 266 may project proximally from the openings 216. In that way, the arms 208, 209 can be disconnected from the connectors 260 by squeezing inwardly on the tabs 266 until their exterior faces 268 disengage the features in the openings 216. Each shaft 262 may also include at least one outwardly projecting boss 270 shaped to be received within a corresponding channel 272 in each opening 216. In that way, the rotational orientation of each docking member 203 with respect to the corresponding arm 208, 209 may be fixed.

Each docking member 203 may include a blade portion 234 and an engagement portion 236. The docking member 203 may be structured to securely engage the respective connecting element 30 at its distal end 274. In that regard, the distal end 274 of the docking member 203 may include one or more (e.g., two) tabs 276 projecting inwardly and structured for engagement with corresponding structures on the exterior surface of the cage 42 of the connecting element 30, as shown in FIG. 8B. Each tab 276, which may be located on the engagement portion 236 of the docking member 203, may be structured to engage a respective recess 278 along an edge 280 of an arm 58 of the cage 42. The tabs 276 may each be positioned on a flexible prong 282 defined by a slot 284 formed in the distal end 274 of the docking member 203. The tabs 276 may each have an angled chamfer 286 on their distal ends to ease insertion of the distal end 274 of the docking member 203 over the cage 42. For example, the chamfer 286 may be arranged such that, as the distal end 274 of the docking member 203 is moved distally over the proximal end 54 of the cage 42, the chamfer 286 will cause the prong 282 to flex outward. Further distal movement of the docking member 203 will move the tabs 276 into engagement with the corresponding recesses 278 of the cage 42. Once the tabs 276 are seated within the recesses 278, the distal end 274 of the docking member 203 will preferably at least somewhat resist unwanted separation of the docking member 203 from the cage 42. That is, lateral surfaces on the proximal ends of the tabs 276 will desirably engage lateral surfaces at the proximal ends of the recesses 278 to prevent the docking member 203 from moving proximally and disengaging the cage 42.

The docking member 203 is preferably also structured to receive the passageway device 31 therein when its distal end 274 is docked to the cage 42 of the connecting element 30. In that regard, the engagement portion 236 may include a tubular body having grooves or channels therein for receiving the blades 56 of the passageway device 31, similar to the tubular bodies disclosed in the '159 application. In another example, as shown in FIGS. 7-8A, the engagement portion 236 may include two blade receivers 238 for receiving a respective one of the two blades 56 of a passageway device 31. The blade receivers 238 may have a similar or identical structure to the blade receivers 138 illustrated in FIG. 4B. In that regard, a cross-section of each docking member 203 in a plane perpendicular to the longitudinal axis 57 of the passageway device 31 may be similar or identical to the plan view of the retraction blade 102 illustrated in FIG. 4B. In an embodiment in which the engagement portion 236 extends distally along the entire passageway device 31 and into engagement with the cage 42 of the connecting element 30, the blade-receiving channels 246 of the blade receivers 238 of the docking member 203 are preferably shaped to receive the wider portions of the blades 56 distally of the steps 71.

To further secure the docking members 203 to the blade-screws 60, the blade receivers 238 of the docking members 203 may include a flexible tab 292 having a boss or protuberance (not shown) extending inwardly therefrom for engaging one of the holes 76 along the length of the blades 56. One blade receiver 238 per docking member 203 may include such a flexible tab 292, as shown in FIG. 7, or both blade receivers 238 of each docking member 203 may include a flexible tab 292.

When the docking members 203 are docked to the respective connecting elements 30 and the blades 56 are positioned in the blade receivers 238, the blade portion 234 of the docking member 203 is desirably positioned alongside the passageway device 31, as shown in FIG. 7, in order to retract adjacent body tissue. In that regard, the blade portion 234 is preferably wider than the passageway device 31 along a direction transverse to the axis 57 of the passageway device 31, and the blade portion 234 may be arcuate along that width dimension. For example, the blade portion 234 may be about 2 to 3 cm wide, while the passageway device 31 of the blade-screw 60 may be about 1 to 1.5 cm wide. The blade portion 234 also preferably extends along a significant portion of the passageway device 31 positioned beneath the skin 51, so as to keep tissue out of the passageway 55 defined between the blades 56. As shown in FIG. 7, the blade portion 234 may extend the entire length of the engagement portion 236 so that the distal end 248 of the blade portion 234 is proximate the cage 42 of the connecting element 30 when the distal end 274 of the docking member 203 is docked to the cage 42. The distal end 248 of the blade portion 234 may be rounded to reduce trauma to the tissue upon insertion of the docking member 203 into the body. For example, the distal end 248 of the blade portion 234 may be shaped similarly to the distal end 148 of the blade portion 134 of the retraction blade 102 illustrated in FIG. 4C. In another embodiment, as shown in FIG. 8A, the distal corners 249 of the blade portion 234 may be rounded. Preferably the docking member 203 is rigid, such that, when the blades 56 are received by the blade receivers 238, the docking member 203 stabilizes the blades 56 and prevents them from prematurely disconnecting from the connecting element 30, particularly when the coupling 72 is not positioned on the blades 56.

In an embodiment in which either or both of the engagement portion 236 and the blade portion 234 extend all the way to the cage 42 of the connecting element 30 when the docking member 203 is docked to the cage 42, the distal end 274 of the docking member 203 may include a slot 288 aligned with the opening 290 defined between the arms 58 of the cage 42. As shown in FIG. 8A, the slot 288 may pass through the distal end 248 of the blade portion 234. Desirably, that slot 288 allows a rod 44 positioned between the arms 58 to extend through the opening 290 and beyond the cage 42 without interference from the blade portion 234.

Although not shown in FIGS. 7-8A, the docking member 203 may also include cutouts and/or a hole similar to those in the retraction blade 102 of FIGS. 3A-6, in order to assist with insertion and removal of the docking member 203. The blade receivers 238 may also be connected together at the proximal end 252 of the docking member 203 in such a way that the engagement portion 236 forms a tubular portion at the proximal end 252.

A system in accordance with an embodiment of the invention may include docking members 203 of different lengths, in order to correspond to different length blade-screws 60 that may be provided with the system. In addition, although not illustrated in the figures, the compression/distraction system 200 of FIGS. 7-8B may be used in conjunction with shafts like those shown in FIGS. 3A-B. Such shafts may be connected directly or indirectly with the manipulation device in order to transfer displacement forces from the manipulation device to the connecting elements 30.

Another embodiment of a compression/distraction system (not shown) may include a retraction blade having a blade portion and an engagement portion. The blade portion may be similar or identical to the blade portion 134 of system 100 or the blade portion 234 of system 200. However, the engagement portion, rather than being structured to engage the passageway devices 31 and/or the connecting elements 30, may be structured to removably secure the retraction blade to one of the couplings 72 (see FIG. 1). For example, the engagement portion may be in the form of a clip at the proximal end of the retraction blade. Preferably the clip would be structured such that, when it is secured to one of the couplings 72, the proximal end of the retraction blade is positioned at least slightly distally of the distal end of the recess 78, so as to not interfere with any contouring or selection of the rod 44 using the recesses 78, as discussed above. Desirably, attachment of such retraction blades to the couplings 72 may allow for increased intraoperative flexibility, by allowing translation of the retraction blades along with the couplings 72 along the length of the blades 56. Such retraction blades may be single-use components and may be made of plastic or polymer, although they may alternatively be made of stainless steel or other biocompatible materials.

Figure 10A:
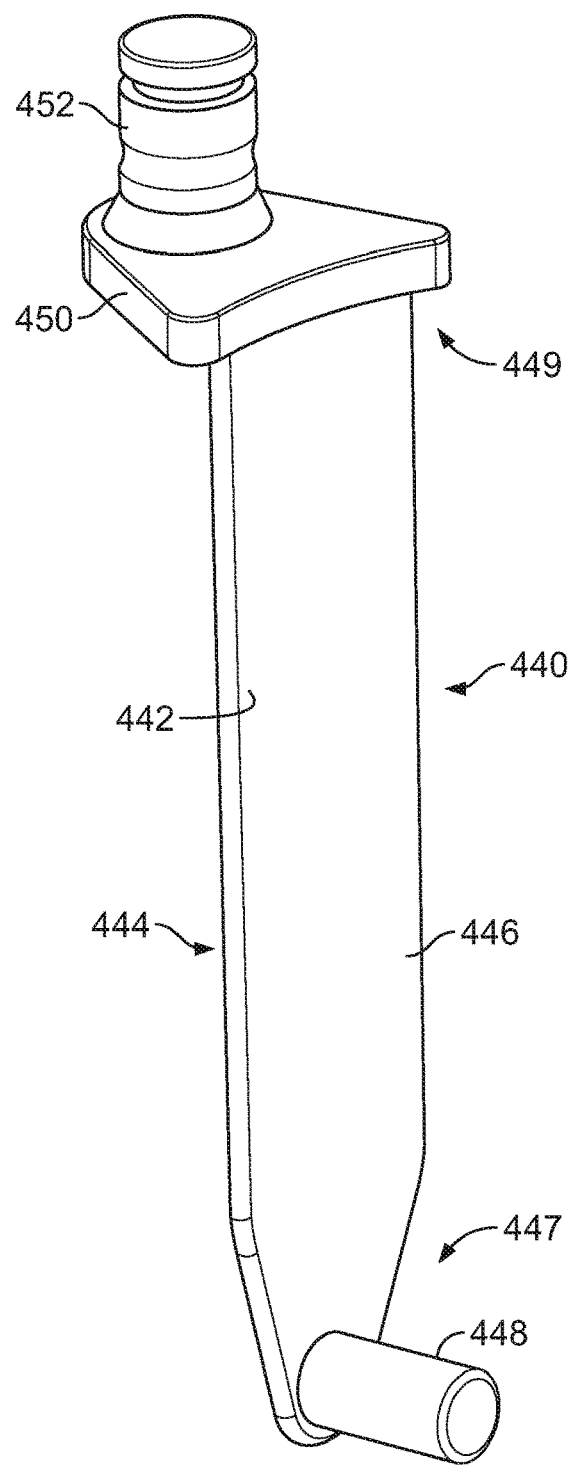
FIG. 10A is a perspective view of a retractor component, in accordance with the embodiment FIG. 10B.

In yet another embodiment of a compression/distraction system, blades (similar to blade portions 134 or 234 of systems 100 or 200, respectively, or similar to the blades of the retractor components disclosed in U.S. Provisional Patent Application No. 61/515,443 ("the '443 application"), filed on Aug. 5, 2011 and entitled "Instrumentation and Method for Spinal Surgery") may themselves transfer the displacement forces (e.g., compression or distraction forces) from the manipulation device to the implanted connecting elements 30. The entire disclosure of the '443 application is hereby incorporated by reference herein as if fully set forth herein. As an example, such a compression/distraction system 400 may include a plurality of retractor components 440, each of which may comprise a blade portion 442 like the vertically elongated blades disclosed in the '443 application. Specifically, as shown in FIG. 10A, each blade portion 442 preferably has an arc-shaped horizontal cross-section, such that the blade portion 442 has a convex tissue-engaging surface 444 and an opposite concave surface 446. Each blade portion 442 is preferably tapered and/or rounded at the distal end 447 of the retractor component 440, which may reduce trauma to the tissue upon insertion of the retractor component 440 into the body. Each retractor component 440 may also include a foot or shaft 448, preferably in the shape of a short cylindrical rod fixed to the blade portion 442, extending laterally (e.g., perpendicularly) from the blade portion 442 adjacent the distal end 447 of the retractor component 440. A proximal end 449 of each retractor component 440 may include a lateral extension or bracket 450, which may be formed as a unit with the blade portion 442. The bracket 450 may extend laterally (e.g., perpendicularly) from the blade portion 442 adjacent the proximal end 449 of the retractor component 440. A connector 452 for connection with a manipulation device may be provided at the proximal end 449 of each retractor component 440, such as on the bracket 450, as shown in FIG. 10A. The connectors 452 might, for example, take the form of a post or they might take the form of the connectors 260 of system 200 discussed above. Although not shown in FIGS. 10A-B, the retractor component 440 may also include cutouts and/or a hole similar to those in the retraction blade 102 of FIGS. 3A-6, in order to assist with insertion and removal of the retractor component 440.

Figure 10B:
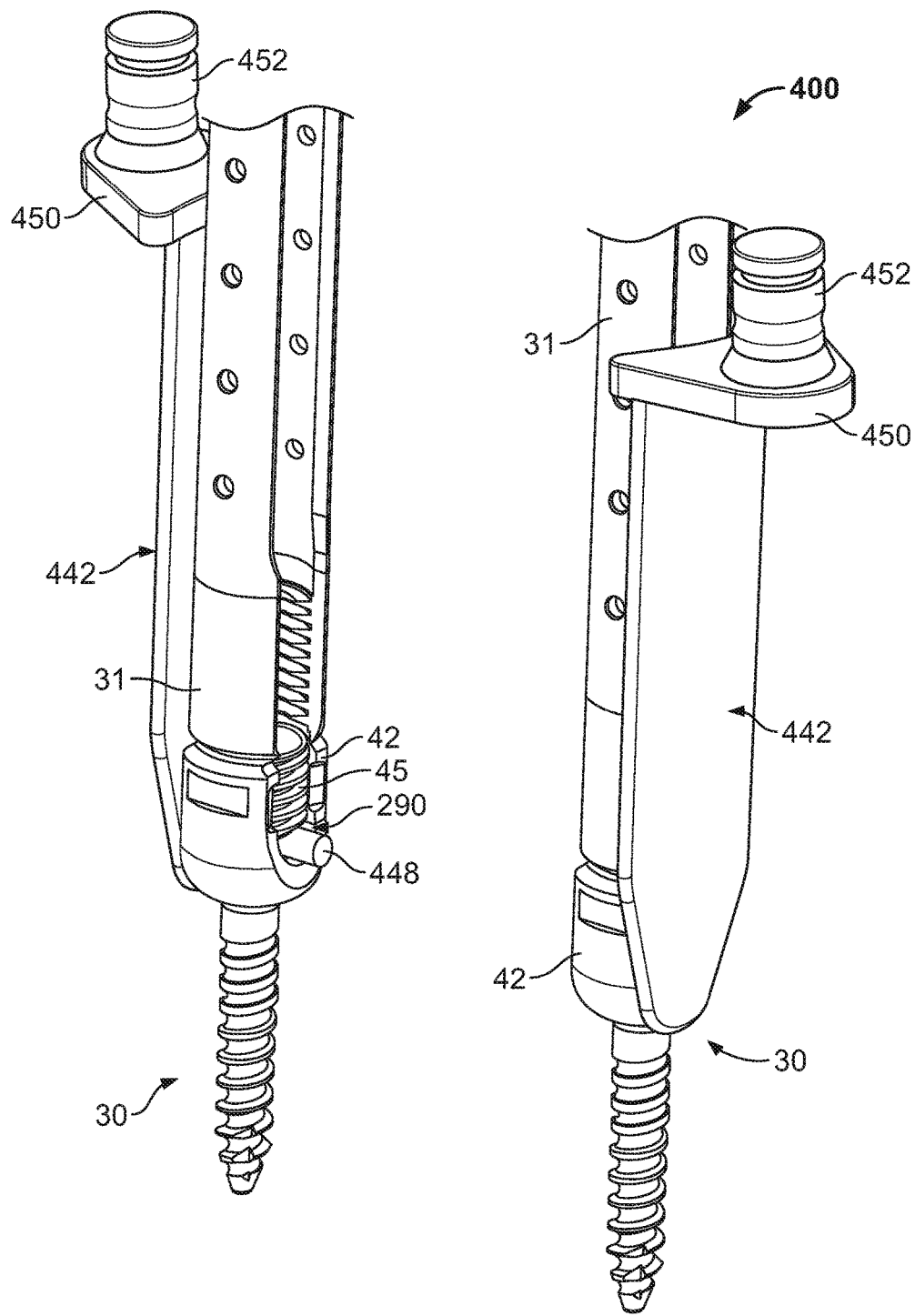
FIG. 10B is a perspective view of components of a compression/distraction system in engagement with a set of blade-screws, in accordance with another embodiment of the present invention

The shaft 448 of each retractor component 440 preferably has the same diameter as that of the spinal fusion rod 44, which the opening 290 defined between the arms 58 of the cage 42 is designed to receive. In that way, the retractor components 440 can be securely engaged with the respective connecting elements 30 by positioning the shafts 448 in the respective openings 290 of the cages 42 of the connecting elements 30 and advancing the set screws 45 along the threads 68 of the cages 42 to secure the shafts 448, and thus the respective retractor components 440, to the cages 42, as shown in FIG. 10B. When the retractor components 440 are engaged with the connecting elements 30 in that manner, the blade portions 442 of the retractor components 440 are preferably positioned alongside the respective passageway devices 31, as shown in FIG. 10B, in order to retract adjacent body tissue. In that regard, each blade portion 442 is preferably wider than the passageway device 31 along a direction transverse to the axis 57 of the passageway device 31. For example, the blade portion 442 may be about 2 to 3 cm wide, while the passageway device 31 of the blade-screw 60 may be about 1 to 1.5 cm wide.

Desirably, firm advancement of the set screws 45 against the shafts 448 of the retractor components 440 will cause the shafts 448 to forcibly press distally against the respective heads 35 of the screws 32. That forcible engagement may force the head 35 of each screw 32 against the cage 42 within which it is received, which may desirably lock the polyaxial movement of the cage 42 with respect to the screw 32. For example, the proximal end of the head 35 of each screw 32 may extend above the distal end of the opening 290 of each cage 42, such that distal movement of the shaft 448 (or the rod 44) positioned within the opening 290 will clamp the screw head 35 between the shaft 448 (or rod 44) and an inner surface of the cage 42. That locking of the polyaxial movement of the connecting elements 30 may be particularly desirable when compressing or distracting the vertebrae.

The retractor components 440 are engageable by a manipulation device (not shown) at connectors 452, such that the manipulation device can move the retractor components 440 towards and away from one another in order to displace the vertebrae to which the connecting elements 30 are connected. The retractor components 440 thus form extenders for transferring displacement forces (e.g., compression and/or distraction forces) from the manipulation device positioned outside the body to the connecting elements 30 connected to vertebrae within the body, to thereby displace the vertebrae with respect to one another. The manipulation device may take any form suitable for engaging the retractor components 440 and displacing them relative to one another. For example, the manipulation device may take the form of the manipulation devices 106, 206 discussed above.

A system in accordance with an embodiment of the invention may include retractor components 440 of different lengths, in order to correspond to different length blade-screws 60 that may be provided with the system.

Figure 9:
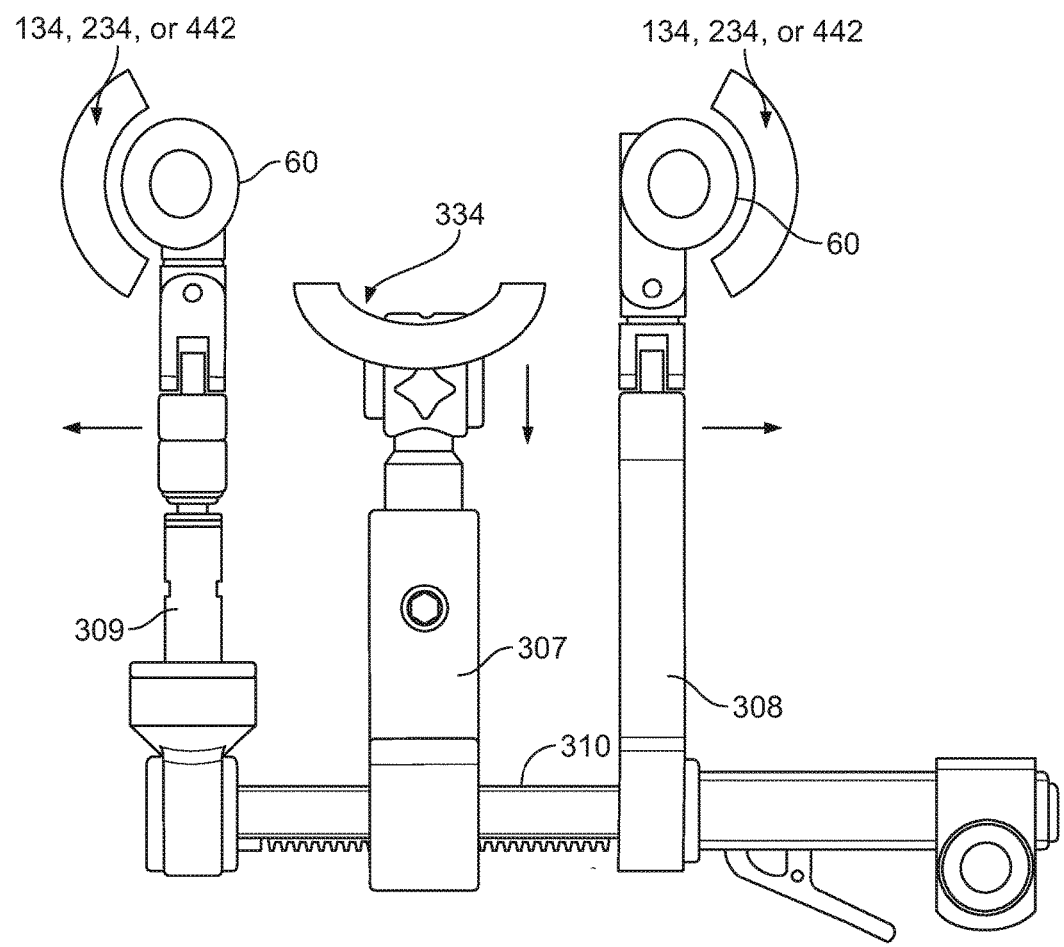
FIG. 9 is a schematic, plan view of an embodiment of a compression/distraction system in engagement with a set of blade-screws, in accordance with another embodiment of the present invention.
Figure 11A:
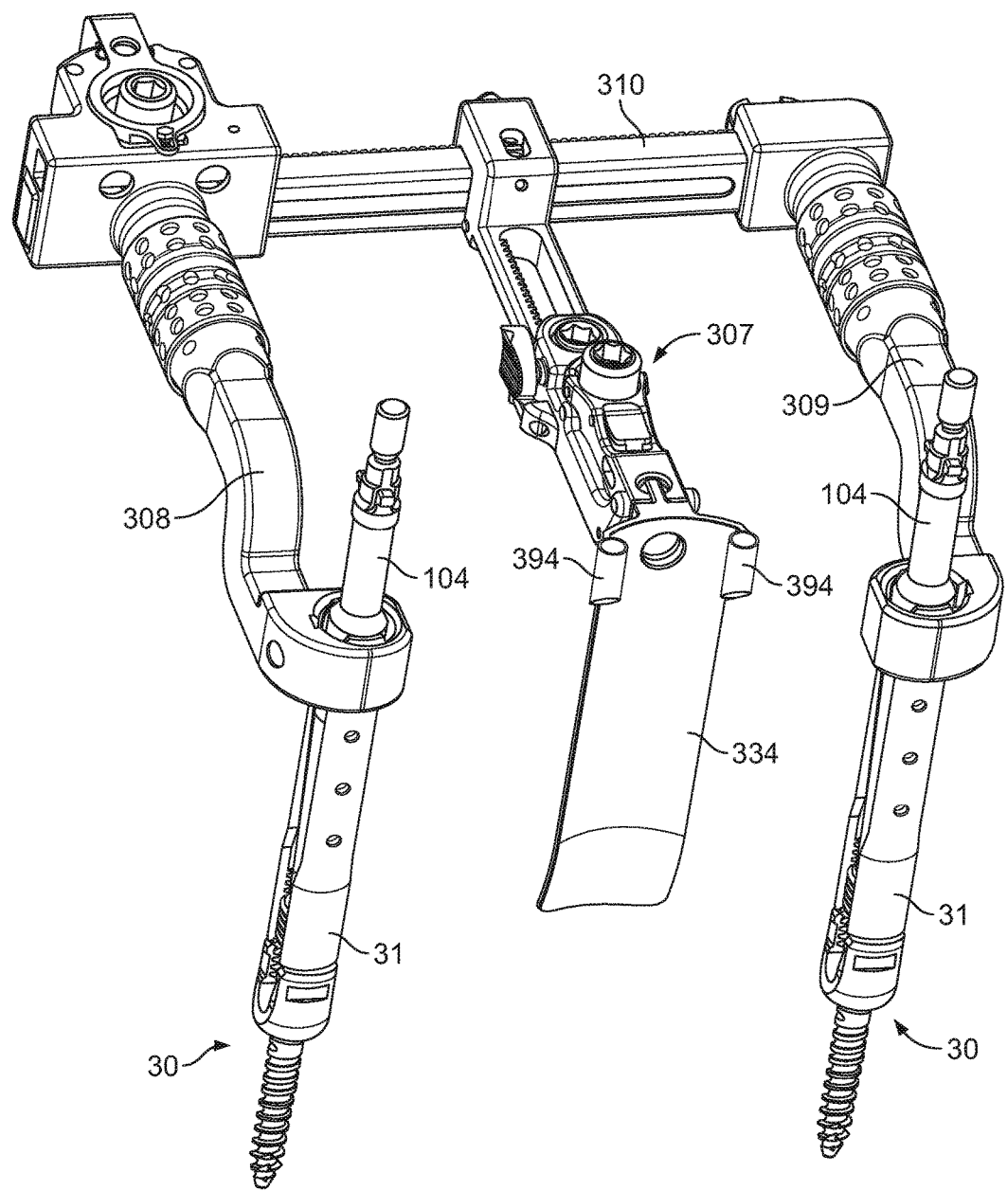
FIG. 11A is a perspective view of an assembly of components of the compression/distraction system of FIG. 9.

Any of the compression/distraction systems (e.g., system 100 of FIGS. 3A-6, system 200 of FIGS. 7-8B, or system 400 of FIGS. 10A-B) may be used in conjunction with additional tissue retraction. That is, in addition to the tissue retraction provided by the blade portions 134, 234, and 442, additional retractor blades may be used. For example, as schematically illustrated in FIG. 9, a manipulation device 306 for use with either or all of system 100, system 200, and system 400 may include an intermediate retractor blade 334 positioned between two adjacent blade-screws 60. The intermediate retractor blade 334 may be supported by an intermediate arm 307, which, as shown in FIG. 9, may be positioned between arms 308 and 309, which are the arms 308, 309 coupled either directly or indirectly to the blade-screws 60. The intermediate arm 307 may extend transversely from the rack 310 of the manipulation device 306. The intermediate arm 307 may be structured to move the intermediate retractor blade 334 along the axis of the intermediate arm 307 (i.e., along the medial/lateral axis 20), and/or the intermediate retractor blade 334 may be pivotable, such that the distal end of the blade 334 can be arranged to retract body tissue further than the proximal end of the blade 334. The intermediate arm 307 may also support a light for providing supplemental illumination of the surgical site. For example, as shown in FIGS. 11A-B, the intermediate retractor blade 334 may include one or more connectors 394 (e.g., one connector 394 on each side of the proximal end of the intermediate retractor blade 334). The connectors 394 may be shaped as hollow, cylindrical components adapted to receive the distal ends of lighting elements 396 (such as fiber optic lighting elements) therein, so as to direct the light from the lighting elements 396 into the surgical site, as shown in FIG. 11B. The manipulation device 306 need not be arranged as illustrated in FIG. 9, however, as any structure may be used which is suitable for engaging (either directly or indirectly) the blade-screws 60 and displacing them relative to one another while also providing an intermediate retractor blade 334 therebetween. Such manipulation devices 306 having intermediate retractor blades 334 may be particularly useful when performing an interbody fusion technique, such as PLIF or TLIF.

In exemplary methods in accordance with embodiments of the present invention, at least two blade-screws 60 may be inserted into the body and connected to adjacent vertebrae, as discussed above. Then, one of the compression/distraction systems discussed above (e.g, systems 100, 200, or 400) may be connected to the blade-screws 60 as follows.

First, with either compression/distraction system 100 or 200, the shafts 104 may be inserted into and threadedly engaged with the respective blade-screws 60, as discussed above. The shafts 104 may not be fully advanced initially, such that the polyaxial movement of the cages 42 with respect to the screws 32 is not yet locked. That may beneficially allow the blade-screws 60 to be moved and/or angled into desirable positions, so as to partially retract the adjacent tissue or otherwise define a desired profile for the adjacent retracted tissue. Such movement and/or angling of the blade-screws 60 may be induced by actuation of the manipulation device. The shafts 104 may then be fully advanced to lock the polyaxial movement of the cages 42 with respect to the screws 32 before distracting the vertebrae to which the connecting elements 30 are connected. Shafts 104 need not be inserted into the blade-screws 60, however, particularly when using the compression/distraction system 200.

Appropriate length components may also be selected by the surgeon or other user. For example, retraction blades 102, docking members 203, or retractor components 440 having respective blade portions 134, 234, 442 with appropriate lengths to the specific anatomy of the patient may be selected.

In the case of compression/distraction system 100, the retraction blades 102 may be advanced into position on the passageway devices 31 of the blade-screws 60. The blade portions 134 are desirably positioned away from one another, as illustrated in FIG. 3A, but each blade portion 134 may be rotated, along with the cage 42 and blades 56 to which it is connected, about the respective screw 52 and into a desired orientation. The arms 108, 109 of the manipulation device 106 may then be securely engaged with the shafts 104.

In the case of the compression/distraction system 200, the docking members 203 may be inserted over the passageway devices 31 of the blade-screws 60 and securely engaged with the connecting elements 30, with the blade portions 234 positioned away from one another, as shown in FIG. 7. The docking members 203 may be inserted with the arms 208, 209 attached to the connectors 260, or the arms 208, 209 of the manipulation device may be engaged with the connectors 260 after the docking members 203 have been inserted.

In the case of compression/distraction system 400, the retractor components 440 may be advanced into position such that the shafts 448 are received in the openings 290 of the cages 42, after which the retractor components 440 may be secured to the cages 42 by advancing set screws 45 into the cages 42 with one or more set screw drivers. When the retractor components 440 are engaged with the connecting elements 30 in that manner, the blade portions 442 of the retractor components 440 may be positioned alongside the respective passageway devices 31, as shown in FIG. 10B. However, the passageway devices 31 may not be positioned alongside the blade portions 442. For example, the passageway devices 31 may be detached from the respective connecting elements 30, either before or after the retractor components 440 are positioned in engagement with the connecting elements 30, in which case the blade portions 442 may provide substantially all of the tissue retraction near the connecting elements 30. The blade portions 442 are desirably positioned away from one another, as illustrated in FIG. 10B, but each retractor component 440 may be rotated, along with the cage 42 to which it is connected, about the respective screw 52 and into a desired orientation. The arms of the manipulation device may then be securely engaged with the connectors 452.

Either before or after the compression/distraction system is installed, an incision I may be made extending from one of the blade-screws 60 to the other. An intermediate retractor blade 334 may then be positioned in the incision I between the blade-screws 60. The intermediate retractor blade 334 may be positioned in the incision I first and then connected to the intermediate arm 307, or the intermediate arm 307 with blade 334 attached to it may be connected to the rack 310 such that the blade 334 is positioned in the incision I. Lighting elements 396 may be connected to the connectors 394 of the intermediate retractor blade 334 either before or after the intermediate retractor blade 334 is positioned in the incision I. After it is positioned in the incision I, the intermediate retractor blade 334 may move in order to open up the incision I and expose a portion of the spine 10 that includes the intervertebral disc between the vertebrae to which the two blade-screws 60 are connected. For example, the intermediate arm 307 may move the intermediate retractor blade 334 along the medial/lateral axis 20 (e.g., towards the rack 310) and/or the intermediate retractor blade 334 may pivot such that the distal end of the blade 334 retracts the body tissue proximate the spine 10 to a larger degree than the retraction of the body tissue proximate the proximal end of the blade 334. Additional tools (such as a Cobb elevator) may be used to help sweep and retract tissue and muscle while positioning the intermediate retractor blade 334 in the incision I and/or while opening up the incision I with the blade 334. The incision I is desirably defined between the intermediate retractor blade 334 and the blade portions 134, 234, or 442. It is noted that having blade portions positioned adjacent to the blade-screws 60 is not necessary, however. For example, when using compression/distraction system 100, the retraction blades 102 may not be used, as shown in FIGS. 11A-B. In that case, as shown in FIG. 11B, the tissue surrounding the surgical site will be held back by the blade-screws 60 themselves, as well as the intermediate retractor blade 334 (if used).

Either before or after the intermediate retractor blade 334 is positioned, the manipulation device may be actuated to displace the vertebrae connected to the blade-screws 60 relative to one another. In particular, the vertebrae may be distracted away from one another, for example to decompress a degenerated intervertebral disc and/or to provide space for the insertion of an interbody implant between the vertebrae. That distraction may also serve to further open up the incision I between the blade-screws 60 by further separating the blade portions 134, 234, or 442. Additionally or alternatively, paddle distractor(s), reamer distractor(s), and/or trial(s), which may be used to size the disc space between the vertebrae, may also be used to create an initial or full distraction of the disc space, after which the manipulation device may be actuated to provide additional distraction, if desired. Once the desired amount of distraction has been achieved, the manipulation device may be locked to maintain the positions of the vertebrae.

An interbody fusion technique, such as PLIF or TLIF, may then be performed through the incision I between the blade-screws 60 and the intermediate retractor blade 334. Such an interbody fusion technique may involve some or all of the steps of: removing portions of vertebral bone (e.g., portions of the lamina and/or facet joints); removing at least a portion of the intervertebral disc; positioning an interbody implant into the intervertebral space; and applying bone graft material to one or more locations in and around the intervertebral space. Examples of interbody implants may be constructed of allograft bone, polyether ether ketone (PEEK), titanium, or other biocompatible materials. Additionally, biologics may be placed in the intervertebral space.

After the interbody implant has been positioned into the intervertebral space, a rod 44 may be inserted into the body and secured within the cages 42 to provide stability to the vertebrae, particularly while the vertebrae fuse. In particular, a rod 44 having the desired contour may be advanced towards the cages 42 of the implanted connecting elements 30 using the passageways 55 through the body tissue provided by the passageway devices 31, until the rod 44 extends between the cages 42. It is noted that the steps of inserting the rod 44 may be performed while the components of one of the compression/distraction systems 100, 200 (including the retraction blade 102 or the docking member 203) are in place over the blade-screws 60. However, at least the shafts 104 may need to be removed before the rod 44 is installed. For example, the shafts 104 may be removed after completion of the interbody fusion technique and before the rod 44 is installed. In the case of compression/distraction system 400, the retractor components 440 may need to be removed (after first removing the set screws 45) in order to free the openings 290 of the cages 42 to receive the rod 44. The interbody implant should provide enough stability, however, to maintain the intervertebral space after the retractor components 440 or shafts 104 have been removed.

Once the rod 44 is positioned within the cages 42, set screws 45 may be inserted into the cages 42. The set screws 45 may be inserted into the passageway devices 31 and advanced along the threads 68 and/or 70 using a set screw driver like that disclosed in the '159 application. The set screw drivers may have a shaft, a proximal driving interface for engagement with a tool for rotating the drivers during advancement, and a distal interface for engagement with an interface (not shown) on set screw 45. For example, the set screw 45 may include a shaped recess (e.g., hexagonal recess) for receiving a correspondingly shaped projection of the distal end of the set screw driver shaft. Multiple set screw drivers may be provided, and each set screw 45 may be inserted with its own corresponding set screw driver. After the set screws 45 are inserted, the set screw driver(s) may be removed.

The set screws 45 may, at first, be only partially advanced along the threads 68 and/or 70, or only one of the set screws 45 may be fully tightened against the rod 44, so that the vertebrae can be further displaced with respect to one another. In particular, the vertebrae may be compressed towards one another using a compression/distraction system, such as system 100 or system 200. In another example, a compression and distraction system such as that disclosed in the '159 application may be used to compress the vertebrae towards one another, in which case the retraction blades 102 or docking members 203 may be removed before inserting such compression and distraction system. If system 100 is used for compression, the shafts 104 may be re-inserted into and threadedly engaged with the respective blade-screws 60. Alternatively, using system 100, the set screw drivers may be left in the passageways 55 defined by the passageway devices 31. The set screw drivers are desirably structured to provide strength to the blade-screws 60 during application of force by the arms of the manipulation device and to help transfer at least some of the force applied by the arms of the manipulation device to the connecting elements 30. For example, the set screw drivers may be sized similarly to the shafts 104, such that the set screw drivers are closely received within the passageways 55 of the blade-screws 60. Thus, when the distal interfaces of the set screw drivers are in engagement with the interfaces of the set screws 45 which have been at least partially engaged with the threads 68 and/or 70 of the blade-screws 60, the set screw drivers may help transfer at least some of the force applied by the arms of the manipulation device to the connecting elements 30. In another alternative, torque wrenches, such as those used for final tightening (discussed below), may be positioned within the passageways 55 to transfer at least some force applied by the manipulation device. Each torque wrench may have a similar structure to the set screw driver, including a shaft, proximal driving interface, and distal interface. The torque wrenches are desirably constructed such that the torque applied by the torque wrench to the set screw 45 is limited to a pre-selected amount (e.g., 8 Nm (newton-meters)). In yet another alternative, one set screw driver and one torque wrench may be positioned in respective passageways 55 of the blade-screws 60 to transfer force from the manipulation device. That arrangement may particularly be used in "one-way" compression, where one of the set screws 45 is tightened and the other is not tightened during compression, such that the non-tightened connecting element 30 is moved along the rod 44 during compression. For example, one of the set screws 45 may be finally tightened with a torque wrench, after which the torque wrench is left in place in the passageway 55 or is replaced by a set screw driver. Then, the set screw 45 for the connecting element on the other side of the intervertebral space being compressed is partially inserted along threads 68 and/or 70 with a set screw driver, after which the set screw driver is left in place in the passageway 55 or is replaced by a torque wrench. Compression may then be performed using the manipulation device, after which the non-tightened set screw 45 may be finally tightened.

Once the vertebrae are located in their intended positions, the set screws 45 may be finally tightened. Such final tightening may be performed by one or more torque wrenches (not shown) in order to ensure that limited torque is applied. In one example, each set screw 45 may be finally tightened with its own corresponding torque wrench. It is noted that the torque wrench(es) may have been inserted earlier and remained in place during one or more steps, such as the step of compressing the vertebrae towards one another.

Either before or after the rod 44 is installed and/or the set screws 45 are finally tightened, the compression/distraction system may be removed from the body. In that regard, the retraction blade 102 or the docking element 203 may be removed by hand or with the use of a tool, for example by using cutouts 154 and/or holes 156 provided on those components as shown in FIGS. 3A-6. The torque wrench(es) may also be removed from the body. Then, the passageway devices 31 can be detached from the respective connecting elements 30 and removed from the body. For example, the blades 56 may be disconnected from the connecting elements 30 by breaking each of the blades 56 away from the connecting elements 30 at the frangible portions 62. One method for breaking the blades 56 of the blade-screw 60 away from the connecting elements is described in the '159 application. Alternatively, if blades 56 separately formed from and detachably connectible to the cages 42 were used, the blades 56 of the passageway devices 31 may be separately disconnected from the connecting elements 30 and removed from the body.

Although various components described herein, such as the retraction blades 102, the shafts 104, and the docking members 203, have been described and illustrated as being designed to interact with the blades 56 of passageway devices 31, it is to be understood that those components could be designed to interact with different types of passageway devices, such as cannulas, towers, or portals, some of which may not have blades 56. In such cases, those components may be designed to interact similarly with those other types of passageway devices. For example, the engagement portions 136 and 236 of the retraction blade 102 and the docking member 203, respectively, may be structured to engage such other types of passageway devices, and the interior surfaces of those engagement portions may have a correspondingly different shape or some other structure(s) for receiving or otherwise engaging corresponding structure(s) of the passageway device. Moreover, the shafts 104 may be structured to be received within such other types of passageway devices.

In addition, although various components have been illustrated and/or described as unitary components having multiple parts or portions, it is noted that, in other embodiments of the invention, such parts or portions could be separate components, which may or may not be connected to one another.

The various components described herein are preferably constructed of materials safe for use in the body. In one embodiment, many of the components to be permanently implanted in the body, such as the blade-screws 60 and the rod 44, may be constructed from titanium or a titanium alloy. In one alternative, some or all of such permanently implantable components may be constructed from a cobalt-chromium alloy, such as the material sold under the trademark VITALLIUM® by Howmedica Osteonics Corp. Some or all of the instruments for use in implanting and manipulating the permanently implantable components, such as the retraction blades 102, the shafts 104, the docking members 203, the retractor components 440, and the components of the manipulation devices 106, 206, 306, may be entirely, largely, or partially constructed from stainless steel.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A retractor device for engaging a connecting element affixed to a vertebra of a spine, the connecting element having a passageway device connected thereto and extending proximally therefrom along a longitudinal axis, the passageway device having an at least partially tubular shape at least partially enclosing a tubular space adapted to receive a spinal fusion rod therein, and the passageway device defining at least one longitudinal opening into the tubular space, the longitudinal opening extending along at least a portion of the longitudinal axis, the retractor device comprising:
   an engagement portion adapted to receive at least a portion of the at least partially tubular shape of the passageway device therein; and
   a retractor blade attached to the engagement portion, the retractor blade having opposing edges in a width dimension orthogonal to a length dimension of the retractor blade, the opposing edges having a longitudinal dimension that extends along the length dimension of the retractor blade, wherein, when the engagement portion receives the passageway device, the length dimension of the retractor blade extends along the longitudinal axis and the opposing edges of the retractor blade project outwardly from the engagement portion along a direction extending away from the longitudinal axis;
   wherein, when the engagement portion receives the passageway device, the retractor blade is positioned such that a solid portion of the retractor blade covers at least a portion of the longitudinal opening.

2. The retractor device of claim 1, wherein the engagement portion is adapted to receive the passageway device such that the engagement portion extends along the passageway device to the connecting element.

3. The retractor device of claim 2, wherein a distal end of the engagement portion is adapted to securely engage the connecting element.

4. The retractor device of claim 3, wherein a proximal end of the retractor device includes a connector for engagement by a manipulation device.

5. The retractor device of claim 1, wherein the passageway device includes a first blade and a second blade, each of the first and second blades having a distal end connected to the connecting element and a proximal end extending proximally therefrom, and wherein the engagement portion includes a first blade receiver and a second blade receiver adapted to receive the respective first and second blades therein.

6. The retractor device of claim 5, wherein an exterior of the engagement portion defines a second longitudinal opening between the first and second blade receivers.

7. A retraction system, comprising:
   the retractor device of claim 5; and
   the passageway device having the first and second blades.

8. The retraction system of claim 7, wherein at least one of the first and second blades changes its width at a step, and wherein, when the first and second blade receivers receive the respective first and second blades, a distal end of the engagement portion is engageable with the step.

9. The retractor device of claim 1, wherein, when the engagement portion receives the passageway device, a distal end of the retractor blade is positioned proximate a proximal end of the connecting element.

10. The retractor device of claim 1, wherein a distal end of the retractor blade is rounded.

11. The retractor device of claim 1, wherein a distal end of the retractor blade includes a slot, and wherein, when the engagement portion receives the passageway device, the slot is aligned with an opening in the connecting element.

12. The retractor device of claim 1, wherein a proximal portion of the retractor device includes at least one gripping portion shaped to be gripped by hand.

13. The retractor device of claim 1, wherein the retractor blade has an arcuate shape.

14. A retraction system, comprising:
   the retractor device of claim 1;
   a second retractor device for engaging a second connecting element affixed to a second vertebra of the spine, the second connecting element having a second passageway device connected thereto and extending proximally therefrom along a second longitudinal axis, the second passageway device defining at least one second longitudinal opening extending along at least a portion of the second longitudinal axis, the second retractor device comprising:
      a second engagement portion adapted to receive at least a portion of a second passageway device therein; and
      a second retractor blade connected to the second engagement portion;
      wherein, when the second engagement portion receives the second passageway device, the second retractor blade is positioned so as to cover at least a portion of the second longitudinal opening;
   a first shaft receivable within the passageway device such that a distal portion of the first shaft is positioned proximate the connecting element and a proximal portion of the first shaft is engageable by a manipulation device; and
   a second shaft receivable within the second passageway device such that a distal portion of the second shaft is positioned proximate the second connecting element and a proximal portion of the second shaft is engageable by the manipulation device;
   wherein the first and second shafts are adapted to transfer a sufficient force to the respective connecting element and second connecting element to displace the vertebra with respect to the second vertebra in response to relative displacement of the first and second shafts induced by the manipulation device.

15. The retraction system of claim 14, wherein the distal portion of the first shaft includes a threaded portion, the threaded portion being engageable with threads in the connecting element or the passageway device.

16. The system of claim 14, further comprising the manipulation device.

17. A retraction system, comprising:
   the retractor device of claim 1;
   a second retractor device for engaging a second connecting element affixed to a second vertebra of the spine, the second connecting element having a second passageway device connected thereto and extending proximally therefrom along a second longitudinal axis, the second passageway device defining at least one second longitudinal opening extending along at least a portion of the second longitudinal axis, the second retractor device comprising:
      a second engagement portion adapted to receive at least a portion of a second passageway device therein; and
      a second retractor blade connected to the second engagement portion;
      wherein, when the second engagement portion receives the second passageway device, the second retractor blade is positioned so as to cover at least a portion of the second longitudinal opening;

wherein a longitudinal length of the retractor blade is different from a longitudinal length of the second retractor blade.

18. The retraction system of claim 17, further comprising a plurality of shafts receivable within a respective one of the passageway devices such that a distal portion of each one of the plurality of shafts is positioned proximate the respective connecting element and a proximal portion of each one of the plurality of shafts is engageable by a manipulation device.

19. The retraction system of claim 18, wherein at least one of the shafts includes a plurality of markings, each of the markings corresponding to a longitudinal length of one of the plurality of retractor devices.

20. The retractor device of claim 1, wherein a longitudinal length of the retractor blade is longer than a longitudinal length of the engagement portion.

\* \* \* \* \*